United States Patent [19]

Ashton et al.

[11] Patent Number: 5,004,747
[45] Date of Patent: Apr. 2, 1991

[54] ISOQUINOLINONES

[75] Inventors: Michael J. Ashton; Andrew W. Bridge, both of Chelmsford; Robert K. Chambers, Little Waltham; Donald I. Dron, Upminster; Garry Fenton, Brentwood; Neil V. Harris, Tilbury; David J. Lythgoe, Gidea Park; Ian M. McFarlane, Dagenham; Christopher G. Newton, Chelmsford; David Riddell, Billericay; Christopher Smith, Benfleet; Keith A. J. Stuttle, Rochford; Malcolm P. Toft, Romford, all of England

[73] Assignee: May & Baker Limited, Dagenham, England

[21] Appl. No.: 494,956

[22] Filed: Mar. 15, 1990

Related U.S. Application Data

[63] Continuation of Ser. No. 302,389, Jan. 26, 1989, abandoned.

[30] Foreign Application Priority Data

Jan. 27, 1988 [GB] United Kingdom ................ 8801772
Aug. 12, 1988 [GB] United Kingdom ................ 8819221

[51] Int. Cl.$^5$ .................. A61K 31/47; C07D 405/06
[52] U.S. Cl. .................................... 514/309; 546/141
[58] Field of Search ........................ 546/141; 514/309

[56] References Cited

U.S. PATENT DOCUMENTS 4,443,607  4/1984  Senda et al. .................... 546/141

Primary Examiner—Glennon H. Hollrah
Assistant Examiner—James H. Turnipseed
Attorney, Agent, or Firm—Morgan & Finnegan

[57] ABSTRACT

Therapeutically useful isoquinolinone derivatives of the formula A—X—R$^3$, wherein A represents a group of the formula:

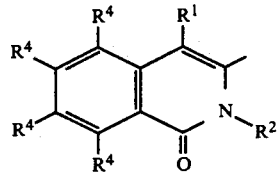

wherein R$^1$ and R$^2$ represents cycloalkyl, alkyl, alkenyl or alkynyl optionally substituted by halogen or cycloalkyl, or represents optionally substituted aryl or heteroaryl, R$^4$ represents hydrogen, halogen, optionally substituted alkyl, alkenyl or alkynyl, optionally substituted aryl or heteroaryl, or a group R$^6$O— wherein R$^6$ represents alkyl, aryl or arylalkyl, X represents ethylene or vinylene, R$^3$ represents a group of the formula:

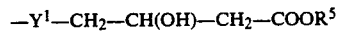

wherein Y$^1$ represents carbonyl, hydroxymethylene or —C(OR)$_2$— wherein R represents alkyl or the two R symbols together represent alkylene and R$^5$ represents hydrogen or optionally substituted alkyl or R$^3$ represents a lactol or lactone ring, and pharmaceutically acceptable salts thereof, processes for their preparation and compositions containing them are described.

17 Claims, No Drawings

ISOQUINOLINONES

This application is a continuation of application Ser. No. 302,389, filed Jan. 26, 1989, now abandoned.

The present invention relates to new therapeutically useful isoquinolinone derivatives, to processes for their preparation, to pharmaceutical compositions containing them, and to their use as pharmaceuticals.

The isoquinolinone derivatives are the compounds of the general formula:

$$A-X-R^3 \qquad \qquad I$$

wherein A represents a group of general formula II shown hereinafter in the present specification, wherein $R^1$ and $R^2$, which may be the same or, preferably, different, each represents a cycloalkyl group containing from 3 to 8 carbon atoms, or represents a straight- or branched-chain alkyl, alkenyl or alkynyl group containing up to 6 carbon atoms, which may be substituted by up to 3 halogen, preferably chlorine or fluorine, atoms, or by a cycloalkyl group containing from 3 to 8 carbon atoms, or represents an optionally substituted aryl, preferably phenyl, or heteroaryl group, and the symbols $R^4$ may be the same or different and each represents a hydrogen or halogen (i.e. fluorine, chlorine, bromine or iodine) atom or represents an optionally substituted straight- or branched-chain alkyl, alkenyl or alkynyl group containing up to 6 carbon atoms, or an optionally substituted aryl, preferably phenyl, or heteroaryl group, or a group of the formula $R^6O-$, wherein $R^6$ represents a straight- or branched-chain alkyl group containing up to 6 carbon atoms, an aryl, e.g. phenyl, group, or an arylalkyl group containing 1 or 2 carbon atoms in the alkyl moiety, e.g. benzyl or phenethyl, X represents an ethylene or vinylene group, preferably a vinylene group in the E-configuration, $R^3$ represents a group of the general formula:

$$-Y^1-CH_2-CH(OH)-CH_2-COOR^5 \qquad \qquad III$$

wherein $Y^1$ represents a carbonyl or hydroxymethylene group or a group of the formula $-C(OR)_2-$ (wherein the symbols R are preferably the same and each represents a straight- or branched-chain alkyl group containing up to 6 carbon atoms, preferably a primary or secondary alkyl group, or together the two symbols R represent a branched or unbranched alkylene chain containing 2 to 5 carbon atoms), and $R^5$ represents a hydrogen atom or an optionally substituted alkyl group containing up to 6 carbon atoms, or $R^3$ represents a lactol or lactone ring of general formula IV shown hereinafter in the specification wherein $Y^2$ represents a carbonyl or hydroxymethylene group, and pharmaceutically acceptable salts thereof when $R^5$ represents a hydrogen atom, for example alkali metal, alkaline earth metal, ammonium and amine salts.

It is to be understood that, where in this specification reference is made to compounds of formula I, it is intended to refer also where the context so permits to their pharmaceutically acceptable salts.

Substituted alkyl, alkenyl or alkynyl groups within the definition of formula I, unless otherwise specified, may carry up to 3 substituents selected from halogen, preferably fluorine or chlorine, atoms and straight- or branched-chain alkoxy and alkylthio groups each containing up to 6 carbon atoms.

Substituted aryl and heteroaryl groups and moieties within the definition of formula I preferably carry one or more substituents selected from halogen, preferably fluorine or chlorine, atoms, cycloalkyl and cycloalkenyl groups each containing from 4 to 8 carbon atoms, optionally substituted straight- or branched-chain alkyl, alkenyl or alkynyl groups each containing up to 6 carbon atoms, and straight- or branched-chain alkoxy groups containing up to 6 carbon atoms.

As will be appreciated by those skilled in the art, the compounds of formula I may exist in various isomeric forms, for example diastereoisomeric forms, and all such forms and mixtures thereof are included within the scope of the invention. However, when $R^3$ represents a group of formula III and $Y^1$ represents a hydroxymethylene group the erythro-form is the preferred form. When $R^3$ represents a group of formula IV the preferred form has the hydroxy group attached to the 4-position of the lactol or lactone ring in the trans-configuration with respect to the rest of the molecule.

Preferably the lactol or lactone ring of formula IV has the (4R, 6S)-configuration when X represents vinylene and the (4R, 6R)-configuration when X represents ethylene.

The compounds of formula I possess useful pharmacological properties, and some are useful as intermediates for the preparation of other therapeutically useful compounds, for example other compounds of formula I, for example as described later in this specification.

For example they lower the concentrations of cholesterol and of low density lipoproteins in the blood. Thus they are of utility in the prevention or treatment of hypercholesterolaemic and hyperlipoproteinaemic states, of atherosclerosis, and of associated conditions such as angina, myocardial infarction, cerebral vascular occlusion, arterial aneurism, peripheral vascular disease, recurrent pancreatitis, xanthomas and fungal infections, e.g. candidiasis.

Particularly important classes of compounds of formula I include those which exhibit one or more of the following features:

(i) one of $R^1$ and $R^2$, preferably $R^1$, represents an optionally substituted aryl or heteroaryl group, more particularly a substituted or unsubstituted phenyl group, for example a phenyl group substituted by a halogen, e.g. chlorine or, more particularly, fluorine, atom, especially in the 4-position of the phenyl group, and/or by one or two straight- or branched-chain alkyl, e.g. methyl, groups or a straight- or branched-chain alkoxy, e.g. methoxy, group, and the other one of $R^1$ and $R^2$, preferably $R^2$, represents a cycloalkyl group containing from 3 to 8 carbon atoms, for example a cyclohexyl group or a straight- or branched-chain alkyl, alkenyl or alkynyl group containing up to 6 carbon atoms, which may be substituted by up to 3 halogen, preferably chlorine or fluorine, atoms or by a cycloalkyl group containing from 3 to 8 carbon atoms, for example a cyclopropylmethyl or cyclohexylmethyl group, more particularly a straight- or branched-chain alkyl group, for example a methyl or isopropyl group;

(ii) X represents a trans-vinylene or ethylene group;

(iii) $R^5$ represents a hydrogen atom or a methyl or ethyl group; and/or (iv) the symbols $R^4$ all represent hydrogen atoms; the other symbols being as hereinbefore defined and, more especially, their pharmaceutically acceptable salts, particularly the alkali metal, e.g. sodium, salts.

Important compounds of formula I include the following:

| | |
|---|---|
| ethyl (E)-3,5-dihydroxy-7-(2-methyl-1-oxo-4-phenyl-1,2-dihydroisoquinolin-3-yl)hept-6-enoate; | A |
| 2:1 mixture of erythro- and threo-diastereoisomers of (E)-3,5-dihydroxy-7-(2-methyl-1-oxo-4-phenyl-1,2-dihydroisoquinolin-3-yl)hept-6-enoic acid; | B |
| and its sodium salt; | BA |
| 4:1 mixture of trans- and cis-diastereoisomers of (E)-4-hydroxy-6-[2-(2-methyl-1-oxo-4-phenyl-1,2-dihydroisoquinolin-3-yl)ethenyl]-3,4,5,6-tetrahydro-2H-pyran-2-one; | C |
| 1:1 mixture of erythro- and threo-diastereoisomers of ethyl (E)-3,5-dihydroxy-7-[4-(4-fluorophenyl)-2-isopropyl-1-oxo-1,2-dihydroisoquinolin-3-yl]hept-6-enoate; | D |
| 4:1 mixture of erythro- and threo-diastereoisomers of (E)-3,5-dihydroxy-7-[4-(4-fluorophenyl)-2-isopropyl-1-oxo-1,2-dihydroisoquinolin-3-yl]hept-6-enoic acid; | E |
| sodium (E)-3,5-dihydroxy-7-[4-(4-fluorophenyl)-2-isopropyl-1-oxo-1,2-dihydroisoquinolin-3-yl]-hept-6-enoate; | F |
| (E)-4-hydroxy-6-[2-{4-(4-fluorophenyl)-2-isopropyl-1-oxo-1,2-dihydroisoquinolin-3-yl}-ethenyl]-3,4,5,6-tetrahydro-2H-pyran-2-one; | G |
| (4R,6S)-(E)-4-hydroxy-6-[2-{4-(4-fluorophenyl)-2-isopropyl-1-oxo-1,2-dihydroisoquinolin-3-yl}-ethen-1-yl]-3,4,5,6-tetrahydro-2H-pyran-2-one; | H |
| (4R,6S)-(E)-4-hydroxy-6-[2-{2-(4-fluorophenyl)-4-isopropyl-1-oxo-1,2-dihydroisoquinolin-3-yl}ethen-1-yl]-3,4,5,6-tetrahydro-2H-pyran-2-one; | I |
| methyl (3R,5S)-(E)-3,5-dihydroxy-7-[4-(4-fluorophenyl)-2-isopropyl-1-oxo-1,2-dihydroisoquinolin-3-yl]hept-6-enoate; | J |
| methyl (3R)-(E)-7-[4-(4-fluorophenyl)-2-isopropyl-1-oxo-1,2-dihydroisoquinolin-3-yl]-3-hydroxy-5-oxohept-6-enoate; | K |
| (2RS,4R,6S)-(E)-2,4-dihydroxy-6-[2-[4-(4-fluorophenyl)-2-isopropyl-1-oxo-1,2-dihydroisoquinolin-3-yl)ethen-1-yl)-3,4,5,6-tetrahydro-2H-pyran; | L |
| (2RS,4R,6S)-(E)-2,4-dihydroxy-6-[2-(2-(4-fluorophenyl)-4-isopropyl-1-oxo-1,2-dihydroisoquinolin-3-yl)ethen-1-yl]-3,4,5,6-tetrahydro-2H-pyran; | M |
| (4R,6S)-(E)-4-hydroxy-6-(2-(2-(4-methoxyphenyl)-4-isopropyl-1-oxo-1,2-dihydroisoquinolin-3-yl)ethen-1-yl)-3,4,5,6-tetrahydro-2H-pyran-2-one; | N |
| (2RS,4R,6S)-(E)-2,4-dihydroxy-6-(2-(4-isopropyl-2-(4-methoxyphenyl)-1-oxo-1,2-dihydroisoquinolin-3-yl)-ethen-1-yl)-3,4,5,6-tetrahydro-2H-pyran; | O |
| (4R,6S)-(E)-6-(2-(2-(4-fluoro-3-methylphenyl)-4-isopropyl-1-oxo-1,2-dihydroisoquinolin-3-yl)ethen-1-yl)-4-hydroxy-3,4,5,6-tetrahydro-2H-pyran-2-one; | P |
| (2RS,4R,6S)-(E)-2,4-dihydroxy-6-(2-(2-(4-fluoro-3-methylphenyl)-4-isopropyl-1-oxo-1,2-dihydroisoquinolin-3-yl)ethen-1-yl)-3,4,5,6-tetrahydro-2H-pyran; | Q |
| (4R,6S)-(E)-6-(2-(2-(4-chlorophenyl)-4-isopropyl-1-oxo-1,2-dihydroisoquinolin-3-yl)ethen-1-yl)-4-hydroxy-3,4,5,6-tetrahydro-2H-pyran-2-one; | R |
| (2RS,4R,6S)-(E)-6-(2-(2-(4-chlorophenyl)-4-isopropyl-1-oxo-1,2-dihydroisoquinolin-3-yl)ethen-1-yl)-2,4-dihydroxy-3,4,5,6-tetrahydro-2H-pyran; | S |
| (4R,6S)-(E)-6-(2-(2-(3,5-dimethylphenyl)-4-isopropyl-1-oxo-1,2-dihydroisoquinolin-3-yl)ethen-1-yl)-4-hydroxy-3,4,5,6-tetrahydro-2H-pyran-2-one; | T |
| (2RS,4R,6S)-(E)-6-(2-(2-(3,5-dimethylphenyl)-4-isopropyl-1-oxo-1,2-dihydroisoquinolin-3-yl)ethen-1-yl)-2,4-dihydroxy-3,4,5,6-tetrahydro-2H-pyran; | U |
| (4R,6S)-(E)-6-(2-(2-(4-fluorophenyl)-4-methyl-1-oxo-1,2-dihydroisoquinolin-3-yl)ethen-1-yl)-4-hydroxy-3,4,5,6-tetrahydro-2H-pyran-2-one; | V |
| (2RS,4R,6S)-(E)-6-(2-(2-(4-fluorophenyl)-4-methyl-1-oxo-1,2-dihydroisoquinolin-3-yl)ethen-1-yl)-2,4-dihydroxy-3,4,5,6-tetrahydro-2H-pyran; | W |
| (4R,6S)-(E)-6-(2-(2-cyclopropylmethyl-4-(4-fluorophenyl)-1-oxo-1,2-dihydroisoquinolin-3-yl)ethen-1-yl)-4-hydroxy-3,4,5,6-tetrahydro-2H-pyran-2-one; | X |
| (2RS,4R,6S)-(E)-6-(2-(2-cyclopropylmethyl-4-(4-fluorophenyl)-1-oxo-1,2-dihydroisoquinolin-3-yl)ethen-1-yl)-2,4-dihydroxy-3,4,5,6-tetrahydro-2H-pyran; | Y |
| (4R,6S)-(E)-6-(2-(2-cyclohexyl-4-isopropyl-1-oxo-1,2-dihydroisoquinolin-3-yl)ethen-1-yl)-4-hydroxy-3,4,5,6-tetrahydro-2H-pyran-2-one; | Z |
| (2RS,4R,6S)-(E)-6-(2-(2-cyclohexyl-4-isopropyl-dihydroxy-3,4,5,6-tetrahydro-2H-pyran; | AA |
| (4R,6S)-(E)-6-(2-(2-cyclohexylmethyl-4-isopropyl-1-oxo-1,2-dihydroisoquinolin-3-yl)ethen-1-yl)-4-hydroxy-3,4,5,6-tetrahydro-2H-pyran-2-one; | AB |
| (2RS,4R,6S)-(E)-6-(2-(2-cyclohexylmethyl-4-isopropyl-1-oxo-1,2-dihydroisoquinolin-3-yl)ethen-1-yl)-2,4-dihydroxy-3,4,5,6-tetrahydro-2H-pyran; | AC |
| (4R,6R)-(E)-4-hydroxy-6-[2-(4-(4-fluorophenyl)-2-isopropyl-1-oxo-1,2-dihydroisoquinolin-3-yl)ethen-1-yl]-3,4,5,6-tetrahydro-2H-pyran-2-one; | AD |
| (2RS,4R,6R)-(E)-2,4-dihydroxy-6-[2-{4-(4-fluorophenyl)-2-isopropyl-1-oxo-1,2-dihydroisoquinolin-3-yl}ethen-1-yl]-3,4,5,6-tetrahydro-2H-pyran; | AE |
| Sodium (3R,5S)-(E)-3,5-dihydroxy-7-[4-(4-fluorophenyl)-2-isopropyl-1-oxo-1,2-dihydroisoquinolin-3-yl)-hept-6-enoate; | AF |
| Sodium (3R,5S)-(E)-3,5-dihydroxy-7-(2-(4-fluorophenyl)-4-isopropyl-1-oxo-1,2-dihydroisoquinolin-3-yl)hept-6-enoate; | AG |
| (4R,6R)-6-[2-{2-(4-fluorophenyl)-4-isopropyl-1-oxo-1,2-dihydroisoquinolin-3-yl}ethyl]-4-hydroxy-3,4,5,6-tetrahydro-2H-pyran-2-one; and | AH |
| (4R,6R)-6-(2-(4-(4-fluorophenyl)-2-isopropyl-1-oxo-1,2-dihydroisoquinolin-3-yl)ethyl)-4-hydroxy-3,4,5,6-tetrahydro-2H-pyran-2-one. | AI |

The letters A to AI and BA are allocated to the compounds for easy reference later in this specification.

Compounds G and, more especially, H and I are of particular importance.

In tests, the compounds of formula I show good results as competitive inhibitors of 3-hydroxy-3-methylglutaryl coenzyme A (HMG CoA) reductase and as a consequence are inhibitors of cholesterol biosynthesis.

For example, in tests the compounds produced inhibition in rat hepatic microsomal HMG CoA reductase activity in vitro as shown in the following Table I.

In the table the concentrations of the test compounds are expressed in micrograms/ml.

TABLE I

| Compound | Concentration | % Inhibition |
|---|---|---|
| B | 20.0 | 65 |
|   | 2.0 | 5 |
| BA | 20.0 | 61 |
|   | 2.0 | 0 |
| D | 20.0 | 94 |
|   | 6.66 | 85 |
|   | 2.22 | 62 |
|   | 0.74 | 35 |
|   | 0.24 | 11 |
| E | 20.0 | 94 |
|   | 6.66 | 82 |
|   | 2.22 | 61 |
|   | 0.74 | 28 |
|   | 0.24 | 15 |
| F | 20.0 | 97 |
|   | 6.66 | 91 |
|   | 2.22 | 80 |
|   | 0.74 | 59 |
|   | 0.24 | 37 |
| G | 20.0 | 97 |
|   | 6.66 | 93 |
|   | 2.22 | 81 |
|   | 0.74 | 58 |
|   | 0.25 | 29 |
|   | 0.082 | 14 |
| H | 20.0 | 100 |
|   | 6.66 | 99 |
|   | 2.22 | 95 |
|   | 0.74 | 85 |
|   | 0.25 | 66 |
|   | 0.082 | 49 |
| I | 2.22 | 96 |
|   | 0.74 | 88 |
|   | 0.25 | 72 |

TABLE I-continued

| Compound | Concentration | % Inhibition |
|---|---|---|
|  | 0.082 | 48 |
|  | 0.0274 | 25 |
| J | 2.22 | 92 |
|  | 0.74 | 79 |
|  | 0.25 | 55 |
|  | 0.082 | 28 |
|  | 0.0274 | 13 |
| M | 20 | 72 |
|  | 6.66 | 56 |
|  | 2.22 | 44 |
|  | 0.74 | 31 |
|  | 0.25 | 18 |
|  | 0.082 | 27 |
| N | 6.66 | 80 |
|  | 2.22 | 59 |
|  | 0.74 | 34 |
|  | 0.25 | 13 |
|  | 0.0824 | 16 |
| P | 20 | 90 |
|  | 6.66 | 90 |
|  | 2.22 | 81 |
|  | 0.74 | 63 |
|  | 0.25 | 39 |
|  | 0.082 | 27 |
| R | 20 | 97 |
|  | 6.66 | 91 |
|  | 2.22 | 78 |
|  | 0.74 | 56 |
|  | 0.25 | 35 |
|  | 0.082 | 21 |
| V | 20 | 85 |
|  | 6.66 | 67 |
|  | 2.22 | 40 |
|  | 0.74 | 10 |
| X | 20 | 96 |
|  | 6.66 | 92 |
|  | 2.22 | 83 |
|  | 0.74 | 61 |
|  | 0.25 | 35 |
|  | 0.082 | 16 |
| Z | 6.66 | 99 |
|  | 2.22 | 96 |
|  | 0.74 | 88 |
|  | 0.25 | 77 |
|  | 0.082 | 50 |
| AB | 6.66 | 66 |
|  | 2.22 | 41 |
|  | 0.74 | 20 |
| AF | 6.66 | 95 |
|  | 2.22 | 93 |
|  | 0.74 | 83 |
|  | 0.25 | 65 |
|  | 0.082 | 38 |
|  | 0.0274 | 15 |
| AG | 2.22 | 96 |
|  | 0.74 | 89 |
|  | 0.25 | 74 |
|  | 0.082 | 57 |
|  | 0.0274 | 15 |
| AH | 20.0 | 91 |
|  | 6.66 | 79 |
|  | 2.22 | 61 |
|  | 0.74 | 47 |
|  | 0.25 | 31 |
|  | 0.082 | 33 |
| AI | 6.66 | 92 |
|  | 2.22 | 81 |
|  | 0.74 | 62 |
|  | 0.25 | 38 |
|  | 0.082 | 16 |

Compounds of formula I and intermediates for their preparation may be prepared by the application or adaptation of known methods, for example methods similar to those described hereinafter in the following Examples and Reference Examples.

Optionally the reactions may be carried out in an inert atmosphere.

For example, according to a feature of the invention, compounds of formula I wherein $R^3$ represents a group of formula III, wherein $Y^1$ represents a hydroxymethylene group and A, $R^5$ and X are as hereinbefore defined, are prepared by the reduction of compounds of the general formula:

$$A-X-R^7 \qquad \qquad V$$

wherein A and X are as hereinbefore defined and $R^7$ represents a group of the general formula:

$$-CH(OH)-CH_2-CO-CH_2-COOR^8 \qquad VI$$

wherein $R^8$ represents an optionally substituted alkyl group containing up to 6 carbon atoms. The reduction may be carried out by means of sodium borohydride, preferably in a lower alkanol, e.g. methanol, and preferably below room temperature, e.g. at or near to 0° C.

According to a further feature of the invention, carboxylic acids of formula I wherein $R^3$ represents a group of formula III wherein $R^5$ represents a hydrogen atom (A, $Y^1$ and X being as hereinbefore defined), or salts thereof, are prepared from the corresponding esters wherein $R^5$ represents an optionally substituted alkyl group containing up to 6 carbon atoms by hydrolysis by known methods, for example by reaction with an aqueous solution of the corresponding base to form the salt, optionally followed by acidification to form the parent carboxylic acid. For instance, alkali metal salts can be prepared by reaction of the esters with aqueous solutions of the appropriate alkali metal hydroxide, preferably in the presence of a lower alkanol, e.g. methanol, as a solvent.

According to a further feature of the invention, compounds of formula I wherein $R^3$ represents a group of formula III, wherein $Y^1$ represents a carbonyl group, A, $R^5$ and X being as hereinbefore defined, are prepared by the oxidation of the corresponding compounds wherein $Y^1$ represents a hydroxymethylene group. The oxidation may be carried out by reaction with activated manganese dioxide, preferably at or near room temperature or, when X represents ethylene, by reaction with pyridinium chlorochromate.

According to a further feature of the invention, compounds of formula I wherein X represents an ethylene group, A and $R^3$ being as hereinbefore defined, are prepared from corresponding compounds wherein X represents a vinylene group by catalytic hydrogenation. Suitable catalysts include those containing palladium, e.g. palladium on charcoal or on calcium carbonate, or mixtures thereof.

According to a further feature of the invention, compounds of formula I wherein $R^3$ represents a lactone ring of formula IV, wherein $Y^2$ represents a carbonyl group, A and X being as hereinbefore defined, are prepared by the cyclisation of the corresponding compounds wherein $R^3$ represents a group of formula III, wherein $Y^1$ represents a hydroxymethylene group and $R^5$ represents a hydrogen atom. Sometimes the cyclisation occurs spontaneously but sometimes it is preferable to warm or to heat the starting material, or to employ a condensing agent. Conveniently the heating is carried out in a solvent such as toluene at temperatures up to the boiling point. Optionally the reaction is carried out in the presence of a trace of an acid, e.g. glacial acetic acid. An example of a suitable condensing agent is dicyclohexylcarbodiimide, which can be used at or near room temperature, in a solvent such as dichloromethane.

According to a further feature of the invention, compounds of formula I wherein $R^3$ represents a lactol ring of formula IV, wherein $Y^2$ represents a hydroxymethylene group, X represents a vinylene group and A is as hereinbefore defined, are prepared by the reaction of compounds of the general formula:

$$[A-CH_2-P(R^9)_3]^+ (Z^1)^- \qquad \text{VII}$$

wherein A is as hereinbefore defined, the groups $R^9$ may be the same or different and each represents a substituted or, preferably, unsubstituted phenyl group, and $(Z^1)^-$ represents a halide, preferably bromide, ion) with compounds of general formula VIII shown hereinafter in the specification (wherein $R^{10}$ and $R^{11}$ each represent suitable protecting groups), to give compounds of general formula IX shown at the end of the specification (wherein A, $R^{10}$ and $R^{11}$ are as hereinbefore defined) which are subjected to acid hydrolysis, for example by treatment with aqueous acetic acid or with p-toluenesulphonic acid in aqueous tetrahydrofuran, to give the said compound of formula I. The protecting groups $R^{10}$ and $R^{11}$ may be the same or, preferably, different. For example, $R^{11}$ can be an alkyl group, preferably unbranched, containing from 1 to 4 carbon atoms, e.g. methyl, and $R^{10}$ can be a silyl group substituted by 3 groups selected from phenyl and alkyl groups, for example a t-butyldimethylsilyl group.

According to a further feature of the invention, compounds of formula I wherein $R^3$ represents a lactone ring of formula IV, wherein $Y^2$ represents a carbonyl group, X represents a vinylene group and A is as hereinbefore defined, are prepared from corresponding compounds of formula I wherein $R^3$ represents a lactol ring of formula IV, wherein $Y^2$ represents a hydroxymethylene group, by selective oxidation, for example by reaction with silver carbonate (in an inert atmosphere and in the dark), manganese dioxide, or an N-haloamide or N-haloimide (e.g. N-iodosuccinimide) in the presence of a tetraalkylammonium halide, e.g. tetraethylammonium iodide or tetrabutylammonium iodide.

The person skilled in the art will observe that the compounds of formula VIII have at least 3 chiral carbon atoms, at positions 2, 4 and 6. By employment of the appropriate diastereoisomer of formula VIII there can be obtained any desired diasteroisomeric form of the product of formula I.

According to a further feature of the invention, compounds of formula I, wherein $R^3$ represents a group of formula III wherein $Y^1$ represents a hydroxymethylene group and $R^5$ represents an optionally substituted alkyl group containing up to 6 carbon atoms, A and X being as hereinbefore defined, are prepared by alcoholysis of corresponding lactones of formula I, wherein $R^3$ represents a group of formula IV, wherein $Y^2$ represents a carbonyl group, using alcohols of the general formula:

$$R^{12}OH \qquad X$$

wherein $R^{12}$ represents an optionally substituted alkyl group containing up to 6 carbon atoms, typically under reflux.

According to a further feature of the invention, compounds of formula I wherein $Y^1$ represents a group of formula $-C(OR)_2-$, R being as hereinbefore defined, are prepared from the corresponding compounds of formula I wherein $Y^1$ represents a carbonyl group, by the application or adaptation of known methods for the preparation of ketals from ketones, for example by reaction with the appropriate alcohols, preferably in the presence of a suitable acid.

According to a further feature of the invention, compounds of formula I wherein $Y^1$ represents a carbonyl group are prepared from the corresponding compounds of formula I wherein $Y^1$ represents a group of formula $-C(OR)_2-$, R being as hereinbefore defined, by the application or adaptation of known methods for the preparation of ketones from ketals, for example by hydrolysis. The hydrolysis is generally carried out by means of an organic acid in the presence of water, for example aqueous acetic acid, or p-toluenesulphonic acid in acetone containing a small amount of water, preferably at temperatures between 5° and 100° C., or alternatively by means of a dilute inorganic acid, for example dilute hydrochloric acid, preferably at temperatures between 0° and 100° C.

The pharmaceutically acceptable salts may be prepared from parent compounds of formula I by known methods, for example by reaction of compounds of formula I (wherein $R^3$ represents a group of formula III in which $R^5$ represents a hydrogen atom) and the appropriate base, e.g. an alkali metal hydroxide or carbonate, an alkaline earth metal oxide, ammonia or an amine, in a suitable solvent which is preferably water in the case of the preparation of alkali and alkaline earth metal salts and water or isopropanol in the case of amine salts.

As well as being useful in themselves as pharmaceutically useful compounds, salts of the compounds of formula I wherein $R^3$ represents a group of formula III wherein $R^5$ represents a hydrogen atom are useful for the purpose of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid, or an organic acid, e.g. acetic acid.

As will be readily appreciated by those skilled in the art, the compounds of formula I, including their aforementioned isomers, may be separated by the application or adaptation of known methods. For example, diastereoisomeric forms may be separated by chromatography using selective adsorption from solution or from the vapour phase onto suitable adsorbents, and enantiomeric forms of compounds of the formula shown in FIG. I wherein $R^3$ represents a group of formula III in which $R^5$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

Compounds of formulae V and VII may be prepared by the application or adaptation of known methods, for example methods illustrated in the following Reference Examples.

By the term "known methods" as used in this specification is meant methods used heretofore or known in the literature. For example, compounds of formula V, wherein A, $R^7$ and X are as previously defined, may be prepared from compounds of the general formula:

$$A-X-CHO \quad\quad XI$$

wherein A and X are as hereinbefore defined, by reaction with a dianion of a compound of the general formula:

$$CH_3COCH_2COOR^8 \quad\quad XII$$

wherein $R^8$ is as hereinbefore defined, generated in situ by treatment with two equivalents of strong base, for example sodium hydride and/or butyl lithium, in a suitable solvent such as tetrahydrofuran and at from $-50°$ C. to $0°$ C.

Compounds of formula XI, wherein A and X are as hereinbefore defined, may be prepared by either:

(a) the oxidation of compounds of the general formula:

$$A-X-CH_2OH \quad\quad XIII$$

wherein A and X are as hereinbefore defined, under conditions similar to those described hereinbefore for the preparation of compounds of formula I wherein $Y^1$ represents a carbonyl group by oxidation; or (b) the reduction of compounds of the general formula:

$$A-X-COZ^2 \quad\quad XIV$$

wherein A and X are as hereinbefore defined and $Z^2$ represents a halogen atom, for example by means of a trialkyltin hydride in the presence of a suitable catalyst, for example a tetrakis(triarylphosphine)palladium[0], in a suitable solvent such as toluene, at from $0°$ C. to $40°$ C.

Compounds of formula XIII, wherein A and X are as hereinbefore defined, may be prepared by the reduction of compounds of formula XIV wherein A, X and $Z^2$ are as hereinbefore defined, for example by means of sodium borohydride or, preferably, lithium borohydride in a suitable solvent such as tetrahydrofuran, and at from $0°$ C. to $50°$ C.

Compounds of formula XIV, wherein A, X and $Z^2$ are as hereinbefore defined, may be prepared from compounds of the general formula:

$$A-X-COOH \quad\quad XV$$

wherein A and X are as hereinbefore defined, for example by means of thionyl chloride, optionally in a suitable solvent, for example toluene, and at from $20°$ C. to $110°$ C.

Compounds of formula XV, wherein A and X are as hereinbefore defined, may be prepared by the hydrolysis of compounds of the general formula:

$$A-X-COOR^{12} \quad\quad XVI$$

wherein A and X are as hereinbefore defined and $R^{12}$ represents an alkyl group containing from 1 to 4 carbon atoms, for example by means of a mixture of glacial acetic acid and concentrated hydrochloric acid, and at from $50°$ C. to $10°$ C.

Compounds of formula XVI wherein X represents a vinylene group, A and $R^{12}$ being as hereinbefore defined, may be prepared from compounds of the general formula:

$$A-CHO \quad\quad XVII$$

wherein A is hereinbefore defined, by a Wittig reaction, or variant thereof, for example by reaction with the anion of a trialkyl phosphonoacetate (generated in situ by treatment with a strong base, for example sodium hydride), in a suitable solvent such as tetrahydrofuran and at from $-20°$ C. to $50°$ C.

Compounds of formula XVI wherein X represents an ethylene group, A and $R^{12}$ being as hereinbefore defined, may be prepared by the catalytic reduction of corresponding compounds wherein X represents a vinylene group, under conditions similar to those described hereinbefore for the preparation of compounds of formula I wherein X represents an ethylene group by catalytic reduction.

Compounds of formula XVII, wherein A is as hereinbefore defined, may be prepared by the oxidation of compounds of the general formula:

$$A-CH_2OH \quad\quad XVIII$$

wherein A is as hereinbefore defined, for example by means of pyridinium chlorochromate in a suitable solvent such as dichloromethane and at from $0°$ C. to $40°$ C.

Compounds of formula XVIII, wherein A is as hereinbefore defined, may be prepared by the reduction of compounds of the general formula:

$$A-COZ^2 \quad\quad XIX$$

wherein A and $Z^2$ are as hereinbefore defined under conditions similar to those described hereinbefore for the preparation of compounds of formula XIII.

Compounds of formula XIX, wherein A and $Z^2$ are as hereinbefore defined, may be prepared from compounds of the general formula:

$$A-COOH \quad\quad XX$$

wherein A is as hereinbefore defined, under conditions similar to those described hereinbefore for the preparation of compounds of formula XIV.

Compounds of formula XX, wherein A is as hereinbefore defined, may be prepared by condensing compounds of the general formula XXI shown hereinafter in the specification, wherein $R^1$ and $R^4$ are as hereinbefore defined, with compounds of the general formula:

$$R^2NH_2 \quad\quad XXII$$

wherein $R^2$ is as hereinbefore defined, optionally in a suitable solvent, for example ethanol or butanol, and at from $50°$ C. to $180°$ C., optionally at elevated pressure.

Compounds of formula XXI, wherein $R^1$ and $R^4$ are as hereinbefore defined, may be prepared by the hydrolysis, decarboxylation and dehydration of compounds of the general formula XXIII shown hereinafter in the specification, wherein $R^1$ and $R^4$ are as hereinbefore defined and $R^{13}$ represents an alkyl group of 1 to 4 carbon atoms, for example in a mixture of glacial acetic acid and concentrated hydrochloric acid, and at from $50°$ C. to $110°$ C.

Compounds of formula XXIII, wherein $R^1$, $R^4$ and $R^{13}$ are as hereinbefore defined, may be prepared by the addition of compounds of the general formula XXIV shown hereinafter in the specification, wherein $R^1$ and $R^4$ are as hereinbefore defined, to compounds of the general formula XXV:

$Z^3CH_2(COOR^{13})_2$  XXV wherein $R^{13}$ is as hereinbefore defined and $Z^3$ represents a halogen atom, for example in the presence of a suitable base, for example potassium tert-butoxide in a suitable solvent such as ethanol, or potassium carbonate in a suitable solvent such as acetone, and at from 30° C. to 80° C.

Compounds of formula XXIV wherein $R^1$ and $R^4$ are as hereinbefore defined can be prepared by the application or adaptation of known methods.

Compounds of formula VII, wherein A, $R^8$ and $Z^1$ are as hereinbefore defined, may be prepared from compounds of the general formula:

A—CH$_2$Z$^1$  XXVI wherein A and $Z^1$ are as hereinbefore defined, by reaction with compounds of the general formula:

$(R^9)_3P$  XXVII wherein $R^9$ is as hereinbefore defined, preferably in a suitable solvent such as toluene, and at from 50° C. to 110° C.

Compounds of formula XXVI, wherein A and $Z^1$ are as hereinbefore defined, may be prepared by halogenation of compounds of the general formula XVIII wherein A is as hereinbefore defined, for example (when $Z^1$ represents a bromine atom, as is preferred) by means of phosphorus tribromide, preferably in a suitable solvent such as diethyl ether, and at from 20° C. to 35° C.

Compounds of formula VIII may be prepared by the application or adaptation of known methods, for example methods described by Rosen et al., J. Org. Chem., 1984, 49, 3994–4003.

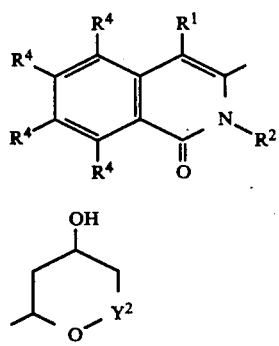

II

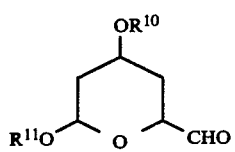

IV

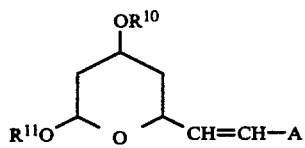

VIII

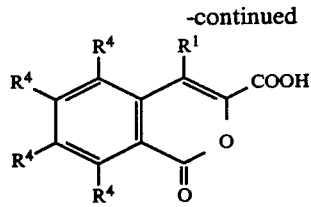

XXI

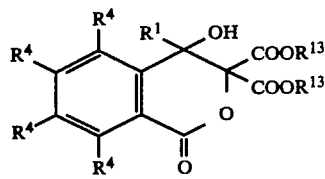

XXIII

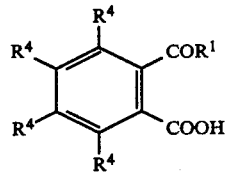

XXIV

The following Examples illustrate the preparation of compounds according to the present invention, and the Reference Examples illustrate the preparation of intermediates.

In the presentation of the nuclear magnetic resonance ("NMR") spectra, "DMSO-d$_6$" means "deuterated dimethylsulphoxide", "d" means "doublet", "m" means "multiplet", "s" means "singlet", "sept" means "septet", "t" means "triplet", "dd" means "doublet of doublets", "b" means "broad", and the positions of the signals are given in parts per million from the tetramethylsilane signal.

EXAMPLE 1

Compound A

A stirred solution of ethyl (E)-5-hydroxy-7-(2-methyl-1-oxo-4-phenyl-1,2-dihydroisoquinolin-3-yl)-3-oxohept-6-enoate (0.35 g; prepared as described hereinafter in Reference Example 1) in methanol (15 ml) at 0° C. was treated with sodium borohydride (0.02 g). The mixture was stirred for one hour and then a further portion of sodium borohydride (0.05 g) was added and stirring was continued for another period of 30 minutes. The resulting clear yellow solution was poured into water (100 ml), forming a white solid. The mixture was extracted with diethyl ether (3×75 ml) and the combined extracts were dried over magnesium sulphate and evaporated, to give ethyl (E)-3,5-dihydroxy-7-(2-methyl-1-oxo-4-phenyl-1,2-dihydroisoquinolin-3-yl)hept-6-enoate (0.35 g) in the form of a yellow solid.

EXAMPLE 2

Compounds B and BA

A solution of ethyl (E)-3,5-dihydroxy-7-(2-methyl-1-oxo-4-phenyl-1,2-dihydroisoquinolin-3-yl)-hept-6-enoate (0.35 g; prepared as described in Example 1) in methanol (15 ml) was cooled to 10° C. and treated with a solution of sodium hydroxide (0.17 g) in water (10 ml) dropwise during 10 minutes. The reaction mixture was warmed to room temperature, stirred for one hour and evaporated to dryness, and the residual solid, which was crude sodium (E)-3,5-dihydroxy-7-(2-methyl-1-oxo-4-phenyl-1,2-dihydroisoquinolin-3-yl)hept-6-enoate, was dissolved in water (50 ml). The aqueous solution was washed with diethyl ether (20 ml) and acidified to pH 5 by treatment with glacial acetic acid. The resulting yellow solid was filtered off and washed well with water, to give (E)-3,5-dihydroxy-7-(2-methyl-1-oxo-4-phenyl-1,2-dihydroisoquinolin-3-yl)hept-6-enoic acid (0.10 g), m.p. 170° C. [Elemental analysis: C, 70.0; H, 5.92; N, 3.37%; calculated: C, 70.2; H, 5.89; N, 3.56%].

The NMR spectrum (DMSO-d6), in particular the signals associated with the proton in the vinyl group geminal to the hydroxymethylene group, indicated that the product was a 2:1 mixture of the erythro- and threo-diastereoisomers.

EXAMPLE 3

Compound C

A stirred mixture of a 2:1 mixture of the erythro- and threo-diastereoisomers of (E)-3,5-dihydroxy-7-(2-methyl-1-oxo-4-phenyl-1,2-dihydroisoquinolin-3-yl)hept-6-enoic acid (0.1 g; prepared as described in Example 2) in dry toluene (10 ml) and glacial acetic acid (2 drops) was heated at reflux for 1 hour. Further quantities of toluene (15 ml) and glacial acetic acid (2 drops) were added and the mixture was heated at reflux for a further period of 3.5 hours. The reaction mixture was cooled to room temperature and concentrated under reduced pressure to half volume. The resulting white solid was filtered off and washed with petroleum ether (b.p. 40°–60° C.), to give (E)-4-hydroxy-6-[2-(2-methyl-1-oxo-4-phenyl-1,2-dihydroisoquinolin-3-yl)ethenyl]-3,4,5,6-tetrahydro-2H-pyran-2-one (0.07 g), m.p. 190°–193° C. [Elemental analysis: C, 71.1; H, 5.52; N, 3.52%; calculated for $C_{23}H_{21}NO_4$: 0.75 $H_2O$: C, 71.0; H, 5.8; N, 3.6%].

The NMR spectrum (DMSO-d6), in particular the signals associated with the proton in the vinyl group geminal to the dihydroisoquinolinyl group, indicated that the product was a 4:1 mixture of the trans- and cis-diastereoisomers.

EXAMPLE 4

Compound D

By proceeding in a manner similar to that hereinbefore described in Example 1, but replacing the ethyl (E)-5-hydroxy-7-(2-methyl-1-oxo-4-phenyl-1,2-dihydroisoquinolin-3-yl)-3-oxohept-6-enoate, used as starting material, by the appropriate quantity of ethyl (E)-7-[4-(4-fluorophenyl)-2-isopropyl-1-oxo-1,2-dihydroisoquinolin-3-yl]-5-hydroxy-3-oxohept-6-enoate (prepared as described in Reference Example 2), there was prepared ethyl (E)-3,5-dihydroxy-7-[4-(4-fluorophenyl)-2-isopropyl-1-oxo-1,2-dihydroisoquinolin-3-yl]hept-6-enoate in the form of a pale yellow oil. [Elemental analysis: C, 69.1; H, 7.0; N, 2.76%; calculated: C, 69.4; H, 6.5; N, 3.0%].

The NMR spectrum (CDCl3), in particular the signals associated with the proton in the vinyl group geminal to the hydroxymethylene group, indicated that the product was a 1:1 mixture of the erythro- and threo-diastereoisomers.

EXAMPLE 5

Compound E

By proceeding in a manner similar to that hereinbefore described in Example 2 but replacing the ethyl (E)-3,5-dihydroxy-7-(2-methyl-1-oxo-4-phenyl-1,2-dihydroisoquinolin-3-yl)hept-6-enoate, used as starting material, by the appropriate quantity of a 1:1 mixture of the erythro- and threo-diastereoisomers of ethyl (E)-3,5-dihydroxy-7-[4-(4-fluorophenyl)-2-isopropyl-1-oxo-1,2-dihydroisoquinolin-3-yl]hept-6-enoate, prepared as described in Example 4, there was prepared (E)-3,5-dihydroxy-7-[4-(4-fluorophenyl)-2-isopropyl-1-oxo-1,2-dihydroisoquinolin-3-yl]hept-6-enoic acid, in the form of a gummy solid.

The NMR spectrum (CDCl3), in particular the signals associated with the proton in the vinyl group geminal to the hydroxymethylene group, indicated that the product was a 1:1 mixture of the erythro- and threo-diastereoisomers.

EXAMPLE 6

Compound F

A solution of a 1:1 mixture of the erythro- and threo-diastereoisomers of ethyl (E)-3,5-dihydroxy-7-[4-(4-fluorophenyl)-2-isopropyl-1-oxo-1,2-dihydroisoquinolin-3-yl]hept-6-enoate (0.18 g; prepared as described in Example 4) in methanol, (10 ml) was treated with aqueous sodium hydroxide solution (2.0M; 0.77 ml) at room temperature. After 90 minutes the solution was evaporated to dryness and the residue was azeotroped on the rotary evaporator with ethyl acetate (2×20 ml). The residue was triturated with diethyl ether (25 ml) and the product was filtered off, to give sodium (E)-3,5-dihydroxy-7-[4-(4-fluorophenyl)-2-isopropyl-1-oxo-1,2-dihydroisoquinolin-3-yl]hept-6-enoate in the form of a pale yellow solid (0.18 g). [Elemental analysis: C, 58.4; H, 5.55; N, 2.62; $H_2O$, 10.0%; calculated for $C_{25}H_{25}O_5NFNa$:3 $H_2O$: C, 58.25; H, 6.06; N, 2.72; $H_2O$, 10.49%].

EXAMPLE 7

Compound G

A solution of a 1:1 mixture of the erythro- and threo-diastereoisomers of (E)-3,5-dihydroxy-7-[4-(4-fluorophenyl)-2-isopropyl-1-oxo-1,2-dihydroisoquinolin-3-yl]hept-6-enoic acid (0.35 g; prepared as described in Example 5) in dichloromethane (25 ml) was treated with dicyclohexylcarbodiimide (0.18 g) and the resulting solution was stirred at room temperature for 1 hour. The solution was treated with water (20 ml), and stirred for 30 minutes. The layers were then separated and the aqueous phase was extracted with dichloromethane (210 ml). The combined extracts were dried over magnesium sulphate and evaporated to dryness. The resulting residue was triturated with diethyl ether (10 ml) and the insoluble material was filtered off. Evaporation of the ethereal solution gave a pale yellow solid, which was triturated with petroleum ether (b.p. 60°–80° C.; 10 ml) and filtered, to give (E)-4-hydroxy-6-[2-{4-(4-fluorophenyl)-2-isopropyl-1-oxo-1,2-dihydroisoquinolin-3-yl}ethenyl]-3,4,5,6-tetrahydro-2H-pyran-2-one, in the form of a pale yellow solid (0.21 g), m.p. 151°–154° C. [Elemental analysis: C, 70.8; H, 5.74; N, 3.35%; calculated: C, 71.24; H, 5.74; N, 3.32%].

The NMR spectrum, in particular the signals associated with the protons on the carbon atom of the tetrahydropyranone ring adjacent to the keto-group, indicated that the product was a 1:1 mixture of the trans- and cis-diastereoisomers.

EXAMPLE 8

Compounds H and L (a) A stirred suspension of [4-(4-fluorophenyl)-2-isopropyl-1-oxo-1,2-dihydroisoquinolin-3-yl]methyltriphenylphosphonium bromide (116 mg; prepared as described in Reference Example 3) in dry tetrahydrofuran (3 ml) was flushed with argon and cooled to −25° C. and treated with a solution of butyllithium in hexanes (1.55M; 0.12 ml) in one portion. The resulting dark red solution was stirred at −25° C. for 30 minutes. The solution was then treated with a solution of methyl 3-O-(t-butyldimethylsilyl)-2,4-dideoxy-6-oxo-α-D-erythro-hexopyranoside (50 mg; prepared by the application of the method of Rosen et al., J. Org. Chem., 1984, 49, 3994–4003) in tetrahydrofuran (1.0 ml) in one portion and the resulting mixture was stirred at −25° C. for 12 hours. The mixture was treated with diethyl ether (5 ml) and allowed to warm to room temperature, and the insolubles were filtered off. Evaporation of the filtrate gave a pale yellow semi-solid (110 mg), which was subjected to flash chromatography on silica gel, using as eluant 10-20% v/v mixtures of ethyl acetate in hexane, to give (2S,4R,6S)-(E)-4-(t-butyldimethylsilyloxy)-6-[2-{4-(4-fluorophenyl)-2-isopropyl-1-oxo-1,2-dihydroisoquinolin-3-yl}ethen-1-yl]-2-methoxy-3,4,5,6-tetrahydro-2H-pyran, in the form of a colourless oil (15 mg).

(b) A solution of (2S,4R,6S)-(E)-4-(t-butyldimethylsilyloxy)-6-[2-{4-(4-fluorophenyl)-2-isopropyl-1-oxo-1,2-dihydroisoquinolin-3-yl}ethen-1-yl]-2-methoxy-3,4,5,6-tetrahydro-2H-pyran [149 mg; prepared as described in Example 8(a)] in a mixture of glacial acetic acid, tetrahydrofuran and water (3:2:2 by volume; 5 ml) was stirred at 70° C. under argon and under a reflux condenser for 3 hours. The resulting clear solution was diluted with diethyl ether (50 ml), washed with water (20 ml) and then with saturated aqueous sodium bicarbonate solution (2×20 ml), dried over magnesium sulphate and evaporated. The resulting residue was subjected to flash chromatography on silica gel, using as eluant ethyl acetate containing from 0 to 50% hexane by volume, to give (2RS,4R,6S)-(E)-2,4-dihydroxy-6-[2-{4-(4-fluorophenyl)-2-isopropyl-1-oxo-1,2-dihydroisoquinolin-3-yl}-ethen-1-yl]-3,4,5,6-tetrahydro-2H-pyran (78 mg) in the form of a white foam.

(c) A mixture of (2RS,4R,6S)-(E)-2,4-dihydroxy-6-[2-{4-(4-fluorophenyl)-2-isopropyl-1-oxo-1,2-dihydroisoquinolin-3-yl}ethen-1-yl]-3,4,5,6-tetrahydro-2H-pyran [162 mg; prepared as described in Example 8(b)] and silver carbonate supported on celite (approximately 1.7 mmoles of $Ag_2CO_3$ per gram; 1.5 g) in benzene (5 ml) was stirred at 80° C. under argon for 3 hours (protected from light). The mixture was then diluted with hot ethyl acetate (25 ml) and filtered through a pad of celite. The filter pad was washed with hot ethyl acetate (25 ml), and the extracts were combined and evaporated to dryness, to give a pale orange oil (130 mg). This oil was subjected to flash chromatography on silica gel, using as eluant diethyl ether containing from 0 to 10% ethyl acetate by volume, to give (4R,6S)-(E)-4-hydroxy-6-[2-{4-(4-fluorophenyl)-2-isopropyl-1-oxo-1,2-dihydroisoquinolin-3-yl}-ethen-1-yl]-3,4,5,6-tetrahydro-2H-pyran-2-one (56 mg), in the form of a beige powder, m.p. 200°–202° C. [Elemental analysis: C, 70.9; H, 5.81; N, 3.21%; calculated: C, 71.2; H, 5.74; N, 3.32%; NMR (in $CDCl_3$): 1.24 and 1.60 (2H, 2 m), 1.66 (6H, d, J=6 Hz), 1.93 (1H, bd), 2.64 (2H, m), 4.16 (1H, bm), 4.63 (1H, m, J=6 Hz), 5.13 (1H, m), 5.49 (1H, dd, J=16 Hz, 5 Hz), 6.41 (1H, dd, J=16 Hz, 4 Hz), 7.00–7.20 (5H, m), 7.40–7.58 (2H, m), 8.45 (1H, m)].

EXAMPLE 9

Compound I

A mixture of (2R,4R,6S)- and (2S,4R,6S)-(E)-2,4-dihydroxy-6-[2-{2-(4-fluorophenyl)-4-isopropyl-1-oxo-1,2-dihydroisoquinolin-3-yl}ethen-1-yl]-3,4,5,6-tetrahydro-2H-pyran (0.2 g; prepared as in Reference Example 4) and silver carbonate supported on celite (approximately 1.7 mmol of $Ag_2CO_3$ per gram; 5.5 g) in toluene (75 ml) was stirred at 80° C. under sufficient vacuum to allow refluxing, with azeotropic removal of water, for 3 hours (the reaction mixture being protected from the light). The mixture was then filtered through a celite pad, the filter pad washed with hot ethyl acetate (2×75 ml) and the combined liquids evaporated to dryness to give a yellow oil, which, upon trituration with diethyl ether gave (4R,6S)-(E)-4-hydroxy-6-[2-{2-(4-fluorophenyl)-4-isopropyl-1-oxo-1,2-dihydroisoquinolin-3-yl}ethen-1-yl]-3,4,5,6-tetrahydro-2H-pyran-2-one in the form of a brown solid, m.p. 207°–209° C. [Elemental analysis: C, 71.1; H, 5.87; N, 3.15%; calculated: C, 71.24; H, 5.74; N, 3.32%; NMR (in $CDCl_3$): 1.25 and 1.68 (2H, m), 1.48 (6H, d, J=7 Hz), 2.40 (1H, bd), 2.56 (2H, m), 3.47 (1H, sept, J=7 Hz), 4.18 (1H, m), 5.1 (1H, m), 5.58 (1H, dd, J=16 Hz, 5 Hz), 6.08 (1H, dd, J=16 Hz, 1.5 Hz), 7.06–7.12 (4H, m), 7.5 (1H, m), 7.69 (1H, m), 8.03 (1H, m), 8.46 (1H, m)].

EXAMPLE 10

Compound J

A solution of (4R,6S)-(E)-4-hydroxy-6-[2-{4-(4-fluorophenyl)-2-isopropyl-1-oxo-1,2-dihydroisoquinolin-3-yl}ethen-1-yl]-3,4,5,6-tetrahydro-2H-pyran-2-one (as prepared in Example 8; 0.5 g) in methanol (400 ml) was refluxed under nitrogen with the exclusion of light for 4 hours. The solution was then allowed to stand for 72 hours, filtered and evaporated to give a pale yellow oil. The last traces of solvent were removed at 40° C. and 0.8 mmHg pressure to give methyl (3R,5S)-(E)-3,5-dihydroxy-7-[4-(4-fluorophenyl)-2-isopropyl-1-oxo-1,2-dihydroisoquinolin-3-yl]hept-6-enoate as a foam [Elemental analysis: C, 68.9; H, 6.4; N, 3.1%, calculated: C, 68.9; H, 6.2; N, 3.1%; NMR (in $CDCl_3$): 0.98–1.30 (2H, m), 1.67 (6H, D, J=8 Hz), 2.41 (2H, m), 3.57 (1H, s), 3.72 (1H, bs), 3.76 (3H, s), 4.08 (1H, m), 4.34 (1H, m), 4.69 (1H, sept, J=8 Hz), 5.45 (1H, dd, J=16 Hz, 6 Hz), 6.33 (1H, dd, J=16 Hz, 1.5 Hz), 6.97–7.56 (7H, m), 8.45 (1H, m)].

EXAMPLE 11

Compound K

A solution of methyl (3R,5S)-(E)-3,5-dihydroxy-7-[4-(4-fluorophenyl)-2-isopropyl-1-oxo-1,2-dihydroisoquinolin-3-yl]hept-6-enoate (as prepared in Example 10; 1.6 g) in dichloromethane (160 ml) was stirred at room temperature under argon with the exclusion of light. Manganese dioxide was added portionwise (4×4 g) over 3 hours and the mixture stirred for a further 17 hours. The mixture was filtered through diatomaceous earth and the filter pad washed with dichloromethane (3×50 ml). The combined filtrate and washings were evaporated to give a viscous orange gum which was purified by flash chromatography on silica gel using diethyl ether as eluant to give methyl (3R)-(E)-7-[4-(4-fluorophenyl)-2-isopropyl-1-oxo-1,2-dihydroisoquinolin-3-yl]-3-hydroxy-5-oxohept-6-enoate as a yellow foam (NMR (in CDCl$_3$): 1.70 (6H, d, J=8 Hz), 2.47 (2H, d, J=6 Hz), 2.58 (2H, m), 3.30 (1H, d, J=4 Hz), 3.76 (3H, s), 4.28–4.58 (2H, m plus sept), 5.99 (1H, d, J=16 Hz), 6.97–7.59 (8H, m), 8.43 (1H, m)].

EXAMPLE 12

Compound M (a) A stirred suspension of [2-(4-fluorophenyl)-4-isopropyl-1-oxo-1,2-dihydroisoquinolin-3-yl]methyltriphenylphosphonium bromide (8.2 g; prepared as described in Reference Example 4) in dry tetrahydrofuran (300 ml) was flushed with argon, cooled to 0° C. and treated dropwise over 10 minutes with a solution of lithium diisopropylamide in tetrahydrofuran (42.5 ml; 0.3M). The resulting deep red solution was stirred for 3 hours at room temperature and was then treated with a solution of methyl 3-O-(tert-butyldimethylsilyl)-2,4-dideoxy-6-oxo-α-D-erythrohexapyranoside (3.5 g) in tetrahydrofuran (20 ml) over 10 minutes and the resulting mixture stirred at room temperature for 18 hours. It was then treated with saturated aqueous ammonium chloride solution (100 ml), diethyl ether (400 ml) and water (100 ml) and the aqueous phase re-extracted with diethyl ether (150 ml). The combined ethereal extracts were washed with water (200 ml) and brine (200 ml), dried over magnesium sulphate and concentrated in vacuo to give a brown oil. This was triturated with diethyl ether (50 ml), the white solid discarded and the ethereal phase concentrated to give crude (2S,4R,6S)-(E)-4-(tert-butyldimethylsilyloxy)-6-[2-{2-(4-fluorophenyl)-4-isopropyl-1-oxo-1,2-dihydroisoquinolin-3-yl}ethen-1-yl]-2-methoxy-3,4,5,6-tetrahydro-2H-pyran in the form of a viscous brown oil.

(b) A solution of crude (2S,4R,6S)-(E)-4-(tert-butyldimethylsilyloxy)-6-[2-{2-(4-fluorophenyl)-4-isopropyl-1-oxo-1,2-dihydroisoquinolin-3-yl}ethen-1-yl]-2-methoxy-3,4,5,6-tetrahydro-2H-pyran (12 g) in a mixture of glacial acetic acid, tetrahydrofuran and water (3:2:2 by volume; 1000 ml) was stirred at 70° C. under argon for 4 hours. The resulting solution was diluted with diethyl ether (200 ml) and washed with water (800 ml). The aqueous phase was extracted with diethyl ether (2×150 ml) and the combined ethereal extracts washed with water (2×200 ml), saturated aqueous sodium hydrogen carbonate solution (4×200 ml) and water (150 ml), dried over magnesium sulphate and evaporated to leave a residue which was purified by flash chromatography on silica gel using diethyl ether as eluant to give a mixture of (2R,4R,6S)- and (2S,4R,6S)-(E)-2,4-dihydroxy-6-[2-{2-(4-fluorophenyl)-4-isopropyl-1-oxo-1,2-dihydroisoquinolin-3-yl}ethen-1-yl]-3,4,5,6-tetrahydro-2H-pyran (1.9 g) in the form of a white foam.

EXAMPLE 13

Compounds N to AG

By proceeding in a manner similar to that described in previous Examples, and using the appropriate intermediates, prepared in a manner similar to that described in the following Reference Examples, there were prepared:

(4R,6S)-(E)-4-hydroxy-6-(2-(4-methoxyphenyl)-4-isopropyl-1-oxo-1,2-dihydroisoquinolin-3-yl)ethen-1-yl)-3,4,5,6-tetrahydro-2H-pyran-2-one, m.p. 202°–203° C. [α]$_D$=+29° (CH$_2$Cl$_2$ at 26° C.). Found: C,72.1; H,6.23; N,3.19%. Required: C,72.1; H,6.24; N,3.23%. [NMR in CDCl$_3$, 1.38–1.79 (2H,m), 1.48 (6H,d,J=8 Hz), 2.39–2.63 (2H,m), 2.66 (1H,d,J=3 Hz), 3.54 (1H,sept,J=8 Hz), 3.82 (3H,s), 4.04 (1H,m), 5.07 (1H,m), 5.58 (1H,dd,J=16 Hz and J=6 Hz), 6.09 (1H,d,J=16 Hz), 6.99 (4H,m), 7.48 (1H,t,J=8 Hz), 7.68 (1H,dt,J=8 Hz and J=1.5 Hz), 8.02 (1H,d,J=8 Hz), 8.47 (1H,dd,J=8 Hz and J=1.5 Hz)];

(2RS,4R,6S)-(E)-2,4-dihydroxy-6-(2-(4-isopropyl-2-(4-methoxyphenyl)-1-oxo-1,2-dihydroisoquinolin-3-yl)ethen-1-yl)-3,4,5,6-tetrahydro-2H-pyran;

(4R,6S)-(E)-6-(2-(2-(4-fluoro-3-methylphenyl)-4-isopropyl-1-oxo-1,2-dihydroisoquinolin-3-yl)ethen-1-yl)-4-hydroxy-3,4,5,6-tetrahydro-2H-pyran-2-one, m.p. 163°–164° C. [α]$_D$=+27° (CH$_2$Cl$_2$ at 25° C.) Found: C,71.9; H,6.16; N,3.17%. Required: C,71.7; H,5.98; N,3.22%. [NMR in CDCl$_3$, 1.28–1.56 (1H,m), 1.48 (6H,d,J=8 Hz), 1.62–1.78 (1H,m), 2.25 (1H,b), 2.30 (3H,s), 2.48–2.70 (2H,m), 3.54 (1H,sept,J=8 Hz), 4.17 (1H,m), 5.11 (1H,m), 5.61 (1H,dd,J=16 Hz and J=6 Hz), 6.11 (1H,b d,J=16 Hz), 6.86–7.14 (3H,m), 7.50 (1H,t,J=8 Hz), 7.69 (1H,dt,J=8 Hz and J=1.5 Hz), 8.03 (1H,d,J=8 Hz), 8.48 (1H,dd,J=8 Hz and J=1.5 Hz)];

(2RS,4R,6S)-(E)-2,4-dihydroxy-6-(2-(2-(4-fluoro-3-methylphenyl)-4-isopropyl-1-oxo-1,2-dihydroisoquinolin-3-yl)ethen-1-yl)-3,4,5,6-tetrahydro-2H-pyran, m.p.200°–202° C. Found: C,71.2; H,6.40; N,3.08%. Required: C,71.4; H,6.41; N,3.20%;

(4R,6S)-(E)-6-(2-(2-(4-chlorophenyl)-4-isopropyl-1-oxo-1,2-dihydroisoquinolin-3-yl)ethen-1-yl)-4-hydroxy-3,4,5,6-tetrahydro-2H-pyran-2-one, m.p.194°–196° C., [α]$_D$=+23.8° (CH$_2$Cl$_2$ at 29° C.) Found: C,68.2; H,5.50; N,3.07; Cl,8.0%. Required: C,68.6; H,5.52; N,3.20; Cl,8.1%. [NMR in CDCl$_3$, 1.47 (6H,d,J=8 Hz), 1.35 (1H,m), 1.68 (1H,m), 2.56 (2H,d,J=5 Hz), 2.76 (1H,b d,J=3 Hz), 3.52 (1H,sept,J=8 Hz), 4.11 (1H,m), 5.09 (1H,m), 5.59 (1H,dd,J=16 Hz and J=6 Hz), 6.11 (1H,dd,J=16 Hz and J=2 Hz), 7.09 (2H,m), 7.37–7.57 (3H,m), 7.70 (1H,m), 8.03 (1H,d,J=8 Hz), 8.46 (1H,m)];

(2RS,4R,6S)-(E)-6-(2-(2-(4-chlorophenyl)-4-isopropyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-(3,5-dimethylphenyl)-4-isopropyl-1-oxo-1,2-dihydroisoquinolin-3-yl)ethen-1-yl)-4-hydroxy-3,4,5,6-tetrahydro-2H-pyran-2-one, m.p.181°–185° C. [α]$_D$=+30.8° C. (CH$_2$Cl$_2$ at 22° C.) Found: C,75.1; H,6.84; N,3.18%. Required: C,75.2; H,6.77; N,3.25%. [NMR in CDCl$_3$, 1.38–1.55 (1H,m), 1.48 (6H,d,J=8 Hz), 1.59–1.68 (1H,m), 2.17 (1H,d,J=4 Hz), 2.32 (6H,s), 2.53 (2H,m), 3.53 (1H,sept,J=8 Hz), 4.01 (1H,m), 5.09 (1H,m), 5.59 (1H,dd,J=16 Hz and J=5 Hz), 6.11 (1H,dd,J=16 Hz and J=1.5 Hz), 6.78 (2H,s), 7.00 (1H,s), 7.49 (1H,m), 7.68 (1H,m), 8.02 (1H,d,J=8 Hz), 8.49 (1H,m)];

(2RS,4R,6S)-(E)-6-(2-(2-(3,5-dimethylphenyl)-4-isopropyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-(4-fluorophenyl)-4-methyl-1-oxo-1,2-dihydroisoquinolin-3-yl)ethen-1-yl)-4-hydroxy-3,4,5,6-tetrahydro-2H-pyran-2-one, m.p.180°–182° C.;

(2RS,4R,6S)-(E)-6-(2-(2-(4-fluorophenyl)-4-methyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-cyclopropylmethyl-4-(4-fluorophenyl)-1-oxo-1,2-dihydroisoquinolin-3-yl)ethen-1-yl)-4-hydroxy-3,4,5,6-tetrahydro-2H-pyran-2-one, m.p.197°–198° C. [α]$_D$=+29.4° (CH$_2$Cl$_2$ at 23° C.) Found: C,71.6; H,5.6; N,3.2%. Required: C,72.0; H,5.6; N,3.2%. [NMR in CDCl$_3$, 0.51 (4H,m), 1.22 (2H,m), 1.63 (1H,m), 2.64 (2H,m), 2.86 (1H,d,J=4 Hz), 4.10 (2H,d,J=7 Hz), 4.20 (1H,m), 5.14 (1H,m), 5.50 (1H,dd,J=16 Hz and J=6 Hz), 6.48 (1H,dd,J=16 Hz and J=1.5 Hz), 7.13 (5H,m), 7.50 (2H,m), 8.45 (1H,m)];

(2RS,4R,6S)-(E)-6-(2-(2-cyclopropylmethyl-4-(4-fluorophenyl)-1-oxo-1,2-dihydroisoquinolin-3-yl)ethen-1-yl)-2,4-dihydroxy-3,4,5,6-tetrahydro-2H-pyran, m.p.198°–201° C. Found: C,71.3; H,6.09; N,3.03%. Required: C,71.7; H,6.02; N,3.22%;

(4R,6S)-(E)-6-(2-(2-cyclohexyl-4-isopropyl-1-oxo-1,2-dihydroisoquinolin-3-yl)ethen-1-yl)-4-hydroxy-3,4,5,6-tetrahydro-2H-pyran-2-one, m.p.150°–151° C. [α]$_D$=+15.1° (CH$_2$Cl$_2$ at 29° C.) Found: C,73.4; H,7.7; N,3.3%. Required: C,73.3; H,7.6; N,3.4%. [NMR in CDCl$_3$, 1.04–1.50 (3H,m), 1.41 (6H,d,J=8 Hz), 1.5–1.76 (3H,m), 1.76–2.02 (3H,m), 2.19 (1H,m), 2.60–2.90 (5H,m), 3.42 (1H,sept,J=8 Hz), 4.04 (1H,m), 4.51 (1H,m), 5.49 (1H,m), 5.80 (1H,dd,J=16 Hz and J=6 Hz), 6.76 (1H,dd,J=16 Hz and J=1.5 Hz), 7.43 (1H,m), 7.60 (1H,m), 7.91 (1H,dd,J=8 Hz), 8.42 (1H,m)];

(2RS,4R,6S)-(E)-6-(2-(2-cyclohexyl-4-isopropyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-cyclohexylmethyl-4-isopropyl-1-oxo-1,2-dihydroisoquinolin-3-yl)ethen-1-yl)-4-hydroxy-3,4,5,6-tetrahydro-2H-pyran-2-one, m.p.141°–142° C. [α]$_D$=+7.8° (CH$_2$Cl$_2$ at 29° C.) Found: C,73.9; H,8.0; N,3.16% Required: C,73.7; H,7.9; N,3.31%. [NMR in CDCl$_3$, 1.44 (6H,d,J=8 Hz), 0.98–2.12 (13H,m), 2.26 (1H,m), 2.83 (2H,m), 3.50 (1H,sept,J=8 Hz), 3.96 (2H,m), 4.53 (1H,m), 5.49 (1H,m), 5.86 (1H,dd,J=16 Hz and J=6 Hz), 6.70 (1H,dd,J=16 Hz and J=1.5 Hz), 7.48 (1H,m), 7.64 (1H,m), 7.96 (1H,d,J=8 Hz), 8.48 (1H,m)];

(2RS,4R,6S)-(E)-6-(2-(2-cyclohexylmethyl-4-isopropyl-1-oxo-1,2-dihydroisoquinolin-3-yl)ethen-1-yl)-2,4-dihydroxy-3,4,5,6-tetrahydro-2H-pyran;

(4R,6R)-(E)-4-hydroxy-6-[2-(4-(4-fluorophenyl)-2-isopropyl-1-oxo-1,2-dihydroisoquinolin-3-yl)ethen-1-yl]-3,4,5,6-tetrahydro-2H-pyran-2-one, m.p.207°–209° C. [α]$_D$=−54° (CH$_2$Cl$_2$ at 29° C.) Found: C,71.0; H,5.47; N,3.37%. Required: C,71.2; H,5.74; N,3.32%. [NMR in CDCl$_3$, 1.16 (1H,m), 1.68 (6H,d,J=8 Hz), 1.88 (1H,m), 2.45 (1H,dd,J=17 Hz and J=8 Hz), 2.58 (1H,d,J=5 Hz), 2.90 (1H,m), 4.22 (1H,m), 4.63 (2H,m), 5.50 (1H,dd,J=16 Hz and J=6 Hz), 6.41 (1H,dd,J=16 Hz), 6.98–7.25 (5H,m), 7.49 (2H,m), 8.42 (1H,m)];

(2RS,4R,6R)-(E)-2,4-dihydroxy-6-[2-{4-(4-fluorophenyl)-2-isopropyl-1-oxo-1,2-dihydroisoquinolin-3-yl}ethen-1-yl]-3,4,5,6-tetrahydro-2H-pyran;

sodium (3R,5S)-(E)-3,5-dihydroxy-7-(4-(4-fluorophenyl)-2-isopropyl-1-oxo-1,2-dihydroisoquinolin-3-yl)hept-6-enoate, m.p.244°–252° C. with decomposition. Found: C,63.0; H,5.5; F,3.53; N,2.87; H$_2$O,3.8%. Required for C$_{25}$H$_{25}$FNNaO$_5$.H$_2$O: C,62.6; H,5.64; F,3.97; N,2.92; H$_2$O,3.8%; and sodium (3R,5S)-(E)-3,5-dihydroxy-7-(2-(4-fluorophenyl)-4-isopropyl-1-oxo-1,2-dihydroisoquinolin-3-yl)hept-6-enoate, m.p.284°–286° C. with decomposition. Found: C,63.8; H,5.48; F,4.5; N,2.82; H$_2$O,1.85%. Required for C$_{25}$H$_{25}$FNNaO$_5$.0.5H$_2$O: C,63.8; H,5.36; F,4.04; N,2.98; H$_2$O,1.91%.

EXAMPLE 14

Compounds AH and AI

A solution of (4R,6S)-(E)-6-[2-{2-(4-fluorophenyl)-4-isopropyl-1-oxo-1,2-dihydroisoquinolin-3-yl}ethen-1-yl]-4-hydroxy-3,4,5,6-tetrahydro-2H-pyran-2-one (0.6 g) in dichloromethane (20 ml) was hydrogenated at atmospheric pressure over 5% palladium on charcoal catalyst for 36 hours. The mixture was diluted with dichloromethane (100 ml) and filtered through diatomaceous earth to remove the catalyst. The filtrate was evaporated to give a gum. The gum was purified by flash chromatography (silica, ethyl acetate as eluent) to give a white solid which was recrystallised from a mixture of cyclohexane and dichloromethane to give (4R,6R)-6-[2-{2-(4-fluorophenyl)-4-isopropyl-1-oxo-1,2-dihydroisoquinolin-3-yl}ethyl]-4-hydroxy-3,4,5,6-tetrahydro-2H-pyran-2-one as a white solid, m.p.192°–193° C. Found: C,70.7; H,6.15; N,3.24%. Required: C,70.9; H,6.15; N,3.31%. [NMR in CDCl$_3$/D$_2$O, 1.20–1.88 (10H,m), 2.30–2.89 (4H,m), 3.46 (1H,sept,J=8 Hz), 4.26 (1H,m), 4.40 (1H,m), 7.24 (4H,m), 7.47 (1H,m), 7.69 (1H,m), 8.03 (1H,d,J=8 Hz), 8.44 (1H,m)].

By proceeding in a similar manner there was prepared (4R,6R)-6-(2-(4-(4-fluorophenyl)-2-isopropyl-1-oxo-1,2dihydroisoquinolin-3-yl)ethyl)-4-hydroxy-3,4,5,6-tetrahydro-2H-pyran-2-one as a white solid, m.p.160°–162° C. [α]$_D$=2° (CH$_2$Cl$_2$ at 29° C.) Found: C,70.9; H,6.3; N,3.33%. Required: C,70.9; H,6.2; N,3.31%. [NMR in CDCl$_3$, 1.41–2.16 (11H,m), 2.26–2.84 (4H,m), 4.31 (1H,m), 4.54 (2H,m), 6.81 (1H,m), 7.22 (4H,m), 7.43 (2H,m), 8.39 (1H,m)].

REFERENCE EXAMPLE 1

(a) A stirred suspension of 2-methyl-1-oxo-4-phenyl-1,2-dihydroisoquinoline-3-carbonyl chloride (5.96 g; prepared according to the method of F. Duro et al., Il. Farmaco Ed. Sci., 36,400) in dry tetrahydrofuran (120 ml) was treated, portionwise, with sodium borohydride (1.68 g) and the mixture was stirred at room temperature for 4 hours. A further portion of sodium borohydride (0.4 g) was then added and the mixture was stirred for a further period of 30 minutes. The reaction mixture was then treated, dropwise, with dilute hydrochloric acid (60 ml; 2N) and then with water (80 ml). The mixture was diluted with diethyl ether (200 ml) and the organic phase was separated, washed with water (2×80 ml), dried over magnesium sulphate and evaporated. The resulting residue was crystallised from ethyl acetate, to give 3-hydroxymethyl-2-methyl-1-oxo-4-phenyl-1,2-dihydroisoquinoline (3.5 g) in the form of white crystals, m.p.159°–161° C. [Elemental analysis: C,77.2; H,5.76; N,5.37%; calculated: C,77.0; H,5.70; N,5.28%].

(b) A stirred suspension of pyridinium chlorochromate (23.36 g) in dichloromethane (250 ml) was treated with a suspension of 3-hydroxymethyl-2-methyl-1-oxo-4-phenyl-1,2-dihydroisoquinoline (19.1 g) in dichloromethane (1000 ml), and stirred for 1.75 hours. Then the reaction mixture was diluted with diethyl ether (3000 ml), stirred for 20 minutes, and filtered through diatomaceous earth. The filter pad was washed with diethyl ether (1000 ml) and the combined filtrate and washings were filtered through a 3 inch thick pad of silica gel. The filtrate was evaporated and the resulting residue was crystallised from ethyl acetate, to give 2-methyl-1-oxo-4-phenyl-1,2-dihydroisoquinolin-3-carbaldehyde (13.22 g) in the form of white crystals, m.p.181°-182° C. [Elemental analysis: C,77.4; H,4.94; N,5.29%; calculated: C,77.6; H,4.98; N,5.32%].

(c) A stirred suspension of sodium hydride (0.564 g; 80% dispersion in mineral oil) in dry tetrahydrofuran (70 ml) under an atmosphere of argon at −12° C., was treated with triethyl phosphonoacetate (4.18 g), dropwise, during 15 minutes. The mixture was stirred at between 0° and 5° C. for 1 hour, and a clear solution was formed. This solution was cooled to −10° C. and treated with a solution of 2-methyl-1-oxo-4-phenyl-1,2-dihydroisoquinoline-3-carbaldehyde (2.8 g) in dry tetrahydofuran (40 ml), dropwise, during 20 minutes. The reaction mixture was stirred at −10° C. for 2.5 hours and then it was allowed to warm to room temperature, and quenched by treatment with saturated aqueous ammonium chloride solution (15 ml). The organic phase was separated and the aqueous phase was extracted with diethyl ether (2×25 ml). The combined organic phases were washed with water (2×25 ml), and dried over magnesium sulphate. Evaporation and crystallisation of the residue from ethyl acetate gave ethyl (E)-3-(2-methyl-1-oxo-4-phenyl-1,2-dihydroisoquinolin-3-yl)propenoate (3.5 g), m.p.163°-165° C. [Elemental analysis: C,74.9; H,5.4; N,3.9%; calculated: C,75.7; H,5.74; N,4.2%].

(d) A solution of ethyl (E)-3-(2-methyl-1-oxo-4-phenyl-1,2-dihydroisoquinolin-3-yl)propenoate (4.0 g) in a mixture of glacial acetic acid (50 ml) and concentrated hydrochloric acid (50 ml) was heated at reflux for 2 hours and then poured onto a mixture of ice and water (100 g). The resulting white solid was filtered off and crystallised from ethanol, to give (E)-3-(2-methyl-1-oxo-4-phenyl-1,2-dihydroisoquinolin-3-yl)propenoic acid (2.8 g) in the form of white crystals, m.p.266°-268° C. [Elemental analysis: C,74.3; H,5.0; N,4.2%; calculated: C,74.7; H,4.95; N,4.59%].

(e) A solution of (E)-3-(2-methyl-1-oxo-4-phenyl-1,2-dihydroisoquinolin-3-yl)propenoic acid (0.92 g) in thionyl chloride (15 ml) was heated at reflux for 4 hours. The excess thionyl chloride was then removed by distillation and the residual yellow solid was washed with petroleum ether (b.p. 40°-60° C.), to give (E)-3-(2-methyl-1-oxo-4-phenyl-1,2-dihydroisoquinolin-3-yl)propenoyl chloride (1.0 g) in the form of a yellow solid, m.p.213°-215° C.

(f) A stirred suspension of (E)-3-(2-methyl-1-oxo-4-phenyl-1,2-dihydroisoquinolin-3-yl)propenoyl chloride (2.0 g) in dry tetrahydrofuran (50 ml) was treated with sodium borohydride (0.25 g) and stirred at room temperature for 12 hours. A further portion of sodium borohydride (0.1 g) was then added and the mixture was stirred for a further period of 18 hours. Yet a further portion of sodium borohydride (0.1 g) was then added and the mixture was stirred for a final period of 2 hours. The mixture was carefully treated with a minimum quantity of dilute hydrochloric acid (2N). The mixture was diluted with diethyl ether (50 ml) and water (30 ml) and the organic phase was separated. The aqueous phase was extracted with diethyl ether (2×50 ml) and the combined organic phases were washed with water (50 ml), dried over magnesium sulphate, and evaporated, to give a yellow solid (2.0 g) which was subjected to flash chromatography on silica gel using ethyl acetate as eluent. The product was crystallised from ethyl acetate, to give (E)-3-(2-methyl-1-oxo-4-phenyl-1,2-dihydroisoquinolin-3-yl)prop-2-en-1-ol (0.3 g) in the form of white crystals, m.p. 209° C.

(g) A stirred solution of (E)-3-(2-methyl-1-oxo-4-phenyl-1,2-dihydroisoquinolin-3-yl)prop-2-en-1-ol (0.4 g) in dry diethyl ether (125 ml) under an atmosphere of nitrogen was treated with activated manganese dioxide (1.8 g). The mixture was stirred for 4 hours. The manganese dioxide was then filtered off and washed well with diethyl ether (4×100 ml) during 15 minutes. The combined ethereal solutions were evaporated, to give (E)-3-(2-methyl-1-oxo-4-phenyl-1,2-dihydroisoquinolin-3-yl)propenal (0.34 g) in the form of a yellow solid, m.p. 228° C.

(h) A stirred suspension of sodium hydride (0.078 g; 80% dispersion in mineral oil) in dry tetrahydrofuran (10 ml) under an atmosphere of nitrogen and at −10° C. was treated with ethyl acetoacetate (0.312 g), dropwise, during 5 minutes. The mixture was stirred for 30 minutes and then it was treated with a solution of butyl lithium in hexane (1 ml; 2.5M) during a period of 5 minutes, whilst maintaining the temperature at −10° C. The mixture was stirred for a further period of 20 minutes at −10° C. and then treated with a solution of (E)-3-(2-methyl-1-oxo-4-phenyl-1,2-dihydroisoquinolin-3-yl)propenal (0.34 g) in dry tetrahydrofuran (30 ml), dropwise, during 15 minutes at −10° C. The mixture was stirred at −10° C. for 2 hours and the resulting red-brown solution was treated with saturated aqueous ammonium chloride solution (15 ml) and then it was poured into a mixture of diethyl ether (75 ml) and water (50 ml). The organic phase was separated and the aqueous phase was extracted with diethyl ether (50 ml). The combined organic phases were washed with water (3×50 ml), dried over magnesium sulphate and evaporated, to give a yellow solid which was subjected to flash chromatography on silica gel, using ethyl acetate as eluent, to give ethyl (E)-5-hydroxy-7-(2-methyl-1-oxo-4-phenyl-1,2-dihydroisoquinolin-3-yl)-3-oxohept-6-enoate (0.35 g) in the form of a yellow solid, m.p.148°-149° C.

REFERENCE EXAMPLE 2

(a) A stirred mixture of 2-(4-fluorobenzoyl)benzoic acid (4.9 g) and tert-butanol (100 ml) was treated with potassium tert-butoxide (2.24 g) at room temperature and the mixture was stirred for 15 minutes. The solvent was then removed on the rotary evaporator and the residue was dissolved in ethanol (200 ml) and treated with diethyl bromomalonate (4.8 g). This mixture was stirred and heated at reflux for 18 hours and then it was evaporated to dryness. The residue was triturated with water (100 ml), to give a white solid, which was filtered off, dried, and crystallised from a mixture of petroleum ether (b.p. 60°-80° C.) and ethyl acetate, to give 3,3-bis-(ethoxycarbonyl)-4-(4-fluorophenyl)-4-hydroxy-3,4-dihydroisocoumarin (3.85 g) in the form of white crystals, m.p.102°-104° C. [Elemental analysis: C,62.6; H,4.72%; calculated: C,62.7; H,4.76%].

(b) A stirred mixture of 3,3-bis(ethoxycarbonyl)-4-(4-fluorophenyl)-4-hydroxy-3,4-dihydroisocoumarin (3.85 g), glacial acetic acid (40 ml) and concentrated hydrochloric acid (40 ml) was heated at reflux for 2 hours. The mixture was then cooled and poured onto a mixture of ice and water (200 ml), and the resulting solid was filtered off and washed with water, to give 4-(4-fluorophenyl)isocoumarin-3-carboxylic acid (2.65 g) in the form of a white powder, m.p.218°-220° C. [Elemental analysis: C,67.4; H,3.41; F,6.73%; calculated: C,67.6; H,3.19; F,6.68%].

(c) A mixture of 4-(4-fluorophenyl)isocoumarin-3-carboxylic acid (59.8 g) and isopropylamine (210 ml) in ethanol (610 ml) was heated in a sealed pressure vessel at 100° C. for 16 hours. The mixture was then evaporated to dryness and the resulting residue was suspended in water (500 ml) and extracted with diethyl ether (100 ml). The layers were separated, and the aqueous layer was acidified to pH1 by treatment with concentrated hydrochloric acid. The precipitate was filtered off, washed with water, and crystallised from aqueous ethanol, to give 4-(4-fluorophenyl)-2-isopropyl-1-oxo-1,2-dihydroisoquinoline-3-carboxylic acid (51.3 g) in the form of white microcrystals, m.p.128°-130° C. [Elemental analysis: C,65.0; H,5.16; N,3.98; F,5.6; $H_2O$, 6.1%; calculated for $C_{19}H_{16}FNO_3 \cdot 1.3H_2O$: C,65.4; H,5.38; N,4.02; F,5.45; $H_2O$, 6.7%].

(d) A mixture of 4-(4-fluorophenyl)-2-isopropyl-1-oxo-1,2-dihydroisoquinoline-3-carboxylic acid (4.9 g) and thionyl chloride (50 ml) was heated at reflux for 90 minutes. The excess thionyl chloride was then removed by evaporation in vacuo (15 mmHg/40° C.) followed three times by treatment with dichloromethane and evaporation in vacuo, to give 4-(4-fluorophenyl)-2-isopropyl-1-oxo-1,2-dihydroisoquinoline-3-carbonyl chloride (4.35 g) in the form of a white solid, m.p.132°-134° C. [Elemental analysis: C,66.4; H,4.4; N,4.04; Cl,10.3%; calculated: C,66.4; H,4.40; N,4.08; Cl,10.31%].

(e)–(h) By proceeding in a manner similar to that hereinbefore described in Example 1 sections (a) to (d) but replacing the 2-methyl-1-oxo-4-phenyl-1,2-dihydroisoquinoline-3-carbonyl chloride, used as a starting material in section (a), by the appropriate quantity of 4-(4-fluorophenyl)-2-isopropyl-1-oxo-1,2-dihydroisoquinoline-3-carbonyl chloride, there were prepared, respectively:

(e) 4-(4-fluorophenyl)-3-hydroxymethyl-2-isopropyl-1-oxo-1,2-dihydroisoquinoline in the form of a white solid, m.p. 110° C. [Elemental analysis: C,72.9; H,5.77; N, 4.53; F,6.32%; calculated: C,73.3; H,5.8; N,4.5; F,6.1%];

(f) 4-(4-fluorophenyl)-2-isopropyl-1-oxo-1,2-dihydroisoquinoline-3-carbaldehyde, in the form of a pale yellow crystalline solid, m.p. 185°-187° C. [Elemental analysis: C,74.1; H,5.2; N,4.8%; calculated: C,73.8; H,5.2; N,4.5%];

(g) ethyl (E)-3-[4-(4-fluorophenyl)-2-isopropyl-1-oxo-1,2-dihydroisoquinolin-3-yl]prop-2-enoate in the form of a white solid, m.p. 99° C. [Elemental analysis: C,72.9; H,6.1; N,3.5%; calculated: C,72.8; H,5.9; N,3.7%]; and (h) (E)-3-[4-(4-fluorophenyl)-2-isopropyl-1-oxo-1,2-dihydroisoquinolin-3-yl]prop-2-enoic acid, in the form of a white solid, m.p.233°-234° C. [Elemental analysis: C,71.6; H,5.15; N,3.84; F,5.21%; calculated: C,71.8; H,5.16; N,3.99; F,5.41%].

(i) A solution of (E)-3-[4-(4-fluorophenyl)-2-isopropyl-1-oxo-1,2-dihydroisoquinolin-3-yl]prop-2-enoic acid (0.35 g) in dry tetrahydrofuran (10 ml) was treated with oxalyl chloride (0.26 ml) and heated at reflux for 2 hours. The solvent was then removed by distillation and the residual yellow solid was washed with petroleum ether (b.p. 40°-60° C.), to give (E)-3-[4-(4-fluorophenyl)-2-isopropyl-1-oxo-1,2-dihydroisoquinolin-3-yl]prop-2-enoyl chloride in the form of a pale yellow solid.

(j) The (E)-3-[4-(4-fluorophenyl)-2-isopropyl-1-oxo-1,2-dihydroisoquinolin-3-yl]prop-2-enoyl chloride, prepared as described in section (i), was dissolved in dry toluene (10 ml). The solution was flushed with nitrogen, and then it was treated with tetrakis(triphenylphosphine)palladium(0) (58 mg). The mixture was then treated with tributyltin hydride (0.27 ml), dropwise, during 5 minutes and the resulting mixture was stirred at room temperature for 90 minutes. The solvent was then evaporated off and the residue was subjected to flash chromatography on silica gel, using ethyl acetate as eluent. The product was triturated with petroleum ether (b.p. 60°-80° C.), to give (E)-3-[4-(4-fluorophenyl)-2-isopropyl-1-oxo-1,2-dihydroisoquinolin-3-yl]prop-2-enal (100 mg) in the form of a yellow solid, m.p. 159°-161° C. [Elemental analysis: C, 75.0; H, 5.44; N, 4.13; F, 5.86%; calculated: C, 75.21; H, 5.41; N, 4.18; F, 5.67%].

(k) By proceeding in a manner similar to that hereinbefore described in Reference Example 1(h), but replacing the (E)-3-(2-methyl-1-oxo-4-phenyl-1,2-dihydroisoquinolin-3-yl)propenal, used as starting material, by the appropriate quantity of (E)-3-[4-(4-fluorophenyl)-2-isopropyl-2-oxo-1,2-dihydroisoquinolin-3-yl]prop-2-enal, there was prepared ethyl (E)-7-[4-(4-fluorophenyl)-2-isopropyl-1-oxo-1,2-dihydroisoquinolin-3-yl]-5-hydroxy-3-oxohept-6-enoate in the form of a pale yellow oil. [Elemental analysis: C, 69.6; H, 6.3; N, 2.78%; calculated: C, 69.7; H, 6.06; N, 3.01%].

REFERENCE EXAMPLE 3

(a) A solution of 4-(4-fluorophenyl)-3-hydroxymethyl-2-isopropyl-1-oxo-1,2-dihydroisoquinoline [5.0 g; prepared as described in Reference Example 2(e)] in diethyl ether (200 ml) was treated with phosphorus tribromide (2.0 ml). The resulting mixture was stirred and heated at reflux for 90 minutes, and then cooled and diluted with diethyl ether (200 ml). The solution was washed with water ($3 \times 50$ ml), dried over magnesium sulphate, and evaporated to dryness, to give 3-bromomethyl-4-(4-fluorophenyl)-2-isopropyl-1-oxo-1,2-dihydroisoquinoline in the form of a white solid (5.8 g), m.p. 116°-119° C.

(b) A solution of 3-bromomethyl-4-(4-fluorophenyl)-2-isopropyl-1-oxo-1,2-dihydroisoquinoline (5.8 g) in toluene (120 ml) was treated with triphenylphosphine (4.1 g), and the resulting mixture was stirred and heated at reflux for 1 hour, during which time a white crystalline solid precipitated from the solution. The solid was filtered off, and washed with petroleum ether (b.p. 60°-80° C.), to give [4-(4-fluorophenyl)-2-isopropyl-1-oxo-1,2-dihydroisoquinolin-3-yl]methyltriphenylphosphonium bromide, in the form of a white crystalline solid (9.64 g), m.p. 274° C.

REFERENCE EXAMPLE 4

(a) A stirred mixture of 2-(2-methylpropanoyl)benzoic acid (44.27 g) and tert-butanol (300 ml) was treated portionwise with potassium tert-butoxide (28.14 g) over 5 minutes at room temperature and the reaction mixture stirred for a further 10 minutes and then treated dropwise over 10 minutes with a solution of diethyl bromomalonate (55.1 g) in ethanol (200 ml). The stirred mixture was refluxed for 18 hours and then evaporated to dryness. The residue was treated with diethyl ether (400 ml) and washed with water (400 ml). The aqueous phase was re-extracted with diethyl ether (200 ml) and the combined ethereal extracts washed with water (200 ml), saturated aqueous sodium hydrogen carbonate solution (200 ml) and water (200 ml), dried over magnesium sulphate and evaporated to give crude 3,3-bis(e- thoxycarbonyl)-4-hydroxy-4-isopropyl-3,4-dihydroisocoumarin (76 g) as an amber oil.

(b) A stirred mixture of crude 3,3-bis(ethoxycarbonyl)-4-hydroxy-4-isopropyl-3,4-dihydroisocoumarin (76 g), glacial acetic acid (500 ml) and concentrated hydrochloric acid (800 ml) was refluxed for 18 hours. The cooled mixture was added to ice/water (3500 ml) and the precipitated solid filtered off and washed with water to give an off-white solid. This was treated with a solution of sodium hydrogen carbonate (40 g) in water (400 ml) and the resultant solution was extracted with diethyl ether (150 ml). The aqueous phase was acidified to pH1 with concentrated hydrochloric acid and the white precipitate filtered off, washed with water and dried at 70° C. to give 4-isopropylisocoumarin-3-carboxylic acid (20.16 g) in the form of a white solid [Elemental analysis: C, 67.4; H, 5.2%; calculated: C, 67.2; H, 5.17%; NMR (in DMSO-$d_6$): 1.45 (6H, d, J=8 Hz), 3.85 (1H, sept, J=8 Hz), 7.6–8.4 (4H, m)].

(c) A suspension of 4-isopropylisocoumarin-3-carboxylic acid (24.68 g) in 4-fluoroaniline (74 ml) was refluxed under argon for 15 minutes. After cooling, the reaction mixture was dissolved in diethyl ether and the resulting solution extracted with aqueous sodium hydroxide (3×300 ml; 1M). The combined aqueous phases were washed with diethyl ether and acidified to pH1 with aqueous hydrochloric acid (2M). The resultant precipitate was filtered, washed with water and dried at 100° C. to give 2-(4-fluorophenyl)-4-isopropyl-1-oxo-1,2-dihydroisoquinoline-3-carboxylic acid (25.2 g) in the form of a white solid, m.p. 276°–277° C. (with decomposition) [Elemental analysis: C, 69.9; H, 4.9; N, 4.3%; calculated: C, 70.15; H, 4.9; N, 4.3%].

(d) A mixture of 2-(4-fluorophenyl)-4-isopropyl-1-oxo-1,2-dihydroisoquinoline-3-carboxylic acid (19.9 g) and thionyl chloride (213 ml) was refluxed for 90 minutes. Excess thionyl chloride was removed in vacuo to give crude 2-(4-fluorophenyl)-4-isopropyl-1-oxo-1,2-dihydroisoquinoline-3-carbonyl chloride (21 g) in the form of a grey/green solid, m.p. 113°–115° C. [Elemental analysis: C, 66.2; H, 4.49; N, 4.06; Cl, 10.8%; calculated: C, 66.4; H, 4.40; N, 4.07; Cl, 10.3%].

(e) A stirred solution of crude 2-(4-fluorophenyl)-4-isopropyl-1-oxo-1,2-dihydroisoquinoline-3-carbonyl chloride (21 g) in dry tetrahydrofuran (300 ml) was treated dropwise with a solution of lithium borohydride in tetrahydrofuran (26 ml; 2.0M) and the mixture stirred at room temperature for 18 hours. The reaction mixture was then treated dropwise with water (50 ml), diethyl ether (500 ml) and more water (200 ml) and the organic layer was separated, washed with water (200 ml) and brine (200 ml), dried over magnesium sulphate and evaporated to leave a yellow oil. This was triturated with a hot mixture of diethyl ether (200 ml) and n-hexane (400 ml) to give 2-(4-fluorophenyl)-3-hydroxymethyl-4-isopropyl-1-oxo-1,2-dihydroisoquinoline (13.7 g) in the form of a white solid, m.p. 157°–158° C. [Elemental analysis: C, 73.1; H, 5.7; N, 4.4%; calculated: C, 73.3; H, 5.8; N, 4.5%; NMR (in CDCl$_3$): 1.55 (7H, d, J=8 Hz,), 3.65 (1H, sept, J=8 Hz), 4.4 (2H, s), 7.1–7.4 (4H, m), 7.5 (1H, t, J=8 Hz,), 7.7 (1H, t, J=8 Hz), 8.04 (1H, d, J=8 Hz), 8.5 (1H, d, J=8 Hz)].

(f) By proceeding in a similar manner to that given in Reference Example 3(a), but replacing the 4-(4-fluorophenyl)-3-hydroxymethyl-2-isopropyl-1-oxo-1,2-dihydroisoquinoline by the appropriate quantity of 2-(4-fluorophenyl)-3-hydroxymethyl-4-isopropyl-1-oxo-1,2-dihydroisoquinoline, there was prepared 3-bromomethyl-2-(4-fluorophenyl)-4-isopropyl-1-oxo-1,2-dihydroisoquinoline in the form of a yellow solid, m.p. 142°–143° C. [Elemental analysis: C, 61.2; H, 4.73; N, 3.74%; calculated: C, 60.9; H, 4.55; N, 3.74%].

(g) By proceeding in a similar manner to that given in Reference Example 3(b), but replacing the 3-bromomethyl-4-(4-fluorophenyl)-2-isopropyl-1-oxo-1,2-dihydroisoquinoline by the appropriate quantity of 3-bromomethyl-2-(4-fluorophenyl)-4-isopropyl-1-oxo-1,2-dihydroisoquinoline, there was prepared [2-(4-fluorophenyl)-4-isopropyl-1-oxo-1,2-dihydroisoquinolin-3-yl]methyltriphenylphosphonium bromide, in the form of a buff solid, m.p. 250°–251° C. (with decomposition).

The present invention includes within its scope pharmaceutical compositions which comprise at least one of the compounds of formula I or a pharmaceutically acceptable salt thereof in association with a pharmaceutically acceptable carrier or coating. In clinical practice the compounds of the present invention may be administered parenterally, for example topically, especially when treating certain fungal infections, but are preferably administered rectally or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilised, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing one or more of the compounds of formula I or a pharmaceutically acceptable salt thereof.

Compositions in the form of solutions or suspensions, if desired together with additives as described above, in vegetable or other greases, paraffin or other waxes or lacquers or creams, to be applied topically, are also included in the invention.

The percentage of active ingredient in the compositions of the invention may be varied, it being necessary that it should constitute a proportion such that a suitable dosage shall be obtained. Obviously, several unit dosage forms may be administered at about the same time. The dose, the route of administration and the duration of the treatment employed will be determined by the physician, and depend upon the desired therapeutic effect and the condition of the patient. In the adult, the doses are generally between 0.1 and 50, preferably between 0.2 and 8.5, mg/kg body weight per day by oral administration.

Compositions for topical administration generally contain up to 5%, preferably from 0.1 to 3%, by weight of active ingredient, and they are normally applied up to four times per day.

The following Example illustrates pharmaceutical compositions according to the present invention.

COMPOSITION EXAMPLE 1

No. 2 size gelatin capsules each containing:

| | |
|---|---|
| (4R,6S-(E)-4-hydroxy-6-[2-{4-(4-fluorophenyl)-2-isopropyl-1-oxo-1,2-dihydroisoquinolin-3yl}ethen-1-yl]-tetrahydropyran-2-one | 20 mg |
| lactose | 100 mg |
| starch | 60 mg |
| dextrin | 40 mg |
| magnesium stearate | 1 mg | were prepared in accordance with the usual procedure.

The active ingredient may be replaced by the appropriate quantity of any other of the compounds of formula I.

We claim:

1. An isoquinolinone derivative of the formula:

$$A-X-R^3 \qquad (I)$$

wherein A represents a group of the formula:

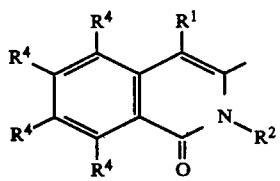

(II)

wherein $R^1$ and $R^2$, which may be the same or different, each represents a cycloalkyl group containing from 3 to 8 carbon atoms, or represents a straight- or branched-chain alkyl, alkenyl or alkynyl group containing up to 6 carbon atoms, which may be substituted by up to 3 halogen atoms or by a cycloalkyl group containing from 3 to 8 carbon atoms, or represents an optionally substituted aryl or heteroaryl group, and the symbols $R^4$ may be the same or different and each represents a hydrogen or halogen atom or represents an optionally substituted straight- or branched-chain alkyl, alkenyl or alkynyl group containing up to 6 carbon atoms, or an optionally substituted aryl or heteroaryl group or a group of the formula $R^6O-$ wherein $R^6$ represents a straight- or branched-chain alkyl group containing up to 6 carbon atoms, an aryl or an arylalkyl group containing 1 or 2 carbon atoms in the alkyl moiety, X represents an ethylene or vinylene group, $R^3$ represents a group of the formula:

$$-Y^1-CH_2-CH(OH)-CH_2-COOR^5 \qquad (III)$$

wherein $Y^1$ represents a carbonyl or hydroxymethylene group or a group of the formula $-C(OR)_2-$ wherein the symbols R each represent a branched or unbranched alkyl group containing up to 6 carbon atoms or together represent a branched or unbranched alkylene chain containing 2 to 5 carbon atoms and $R^5$ represents a hydrogen atom or an optionally substituted alkyl group containing up to 6 carbon atoms, or $R^3$ represents a lactol or lactone ring of the formula:

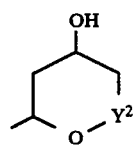

(IV)

wherein $Y^2$ represents a carbonyl or hydroxymethylene group, or a pharmaceutically acceptable salt thereof when $R^5$ represents a hydrogen atom.

2. A compound according to claim 1 wherein $R^1$ and $R^2$ are different.

3. A compound according to claim 1 wherein X represents a vinylene group in the E-configuration.

4. A compound according to claim 1 wherein aryl groups are phenyl and arylalkyl groups are phenylalkyl.

5. A compound according to claim 1 wherein halogen substituents on alkyl, alkenyl or alkynyl groups are chlorine or fluorine atoms.

6. A compound according to claim 1 wherein optionally substituted alkyl, alkenyl or alkynyl groups carry up to 3 substituents selected from halogen atoms and straight- or branched-chain alkoxy and alkylthio groups each containing up to 6 carbon atoms and substituted aryl and heteroaryl groups carry one or more substituents selected from halogen atoms, cycloalkyl and cycloalkenyl groups each containing from 4 to 8 carbon atoms, optionally substituted straight- or branched-chain alkyl, alkenyl or alkynyl groups each containing up to 6 carbon atoms, and straight- or branched-chain alkoxy groups each containing up to 6 carbon atoms.

7. A compound according to claim 1 wherein $R^3$ represents a group of formula III, $Y^1$ represents a hydroxymethylene group and the compound is in the erythro-form.

8. A compound according to claim 1 wherein $R^3$ represents a group of formula IV and the hydroxy group attached to the 4-position of the lactol or lactone ring is in the trans-configuration with respect to the rest of the molecule.

9. A compound according to claim 1 wherein $R^3$ represents a group of the formula IV which has the (4R,6S)-configuration when X represents vinylene and the (4R,6R)-configuration when X represents ethylene.

10. A compound according to claim 1 which comprises one or more of the following features:

(i) one of $R^1$ and $R^2$ represents an optionally substituted aryl or heteroaryl group and the other represents a cycloalkyl group containing from 3 to 8 carbon atoms or a straight- or branched-chain alkyl, alkenyl or alkynyl group containing up to 6 carbon atoms, which may be substituted by up to 3 halogen atoms, or by a cycloalkyl group containing from 3 to 8 carbon atoms;

(ii) X represents a trans-vinylene or ethylene group;
(iii) R⁵ represents a hydrogen atom or a methyl or ethyl group; and/or
(iv) the symbols R⁴ all represent hydrogen atoms.

11. A compound according to claim 10 wherein R¹ represents a substituted or unsubstituted phenyl group and R² represents a cyclohexyl group, a straight- or branched-chain alkyl group or a cyclopropylmethyl or cyclohexylmethyl group.

12. A compound according to claim 10 which is a pharmaceutically acceptable salt.

13. A compound according to claim 1 which is (E)-4-hydroxy-6-[2-{4-(4-fluorophenyl)-2-isopropyl-1-oxo-1,2-dihydroisoquinolin-3-yl}ethenyl]-3,4,5,6-tetrahydro-2H-pyran-2-one.

14. A compound according to claim 1 which is (4R,6S)-(E)-4-hydroxy-6-[2-{4-(4-fluorophenyl)-2-isopropyl-1-oxo-1,2-dihydroisoquinolin-3-yl}-ethen-1-yl]-3,4,5,6-tetrahydro-2H-pyran-2-one.

15. A compound according to claim 1 which is (4R,6S)-(E)-4-hydroxy-6-[2-{2-(4-fluorophenyl)-4-isopropyl-1-oxo-1,2-dihydroisoquinolin-3-yl}ethen-1-yl]-3,4,5,6-tetrahydro-2H-pyran-2-one.

16. A compound according to claim 1 which is a compound selected from the group consisting of ethyl (E)-3,5-dihydroxy-7-(2-methyl-1-oxo-4-phenyl-1,2-dihydroisoquinolin-3-yl)hept-6-enoate;

(E)-3,5-dihydroxy-7-(2-methyl-1-oxo-4-phenyl-1,2-dihydroisoquinolin-3-yl)hept-6-enoic acid; and its sodium salt;

(E)-4-hydroxy-6-[2-(2-methyl-1-oxo-4-phenyl-1,2-dihydroisoquinolin-3-yl)ethenyl]-3,4,5,6-tetrahydro-2H-pyran-2-one;

ethyl (E)-3,5-dihydroxy-7-[4-(4-fluorophenyl)-2-isopropyl-1-oxo-1,2-dihydroisoquinolin-3-yl]hept-6-enoate;

(E)-3,5-dihydroxy-7-[4-(4-fluorophenyl)-2-isopropyl-1-oxo-1,2-dihydroisoquinolin-3-yl]hept-6-enoic acid;

sodium (E)-3,5-dihydroxy-7-[4-(4-fluorophenyl)-2-isopropyl-1-oxo-1,2-dihydroisoquinolin-3-yl]hept-6-enoate;

methyl (3R,5S)-(E)-3,5-dihydroxy-7-[4-(4-fluorophenyl)-2-isopropyl-1-oxo-1,2-dihydroisoquinolin-3-yl]hept-6-enoate;

methyl (3R)-(E)-7-[4-(4-fluorophenyl)-2-isopropyl-1-oxo-1,2-dihydroisoquinolin-3-yl]-3-hydroxy-5-oxohept-6-enoate;

(2RS,4R,6S)-(E)-2,4-dihydroxy-6-(2-[4-(4-fluorophenyl)-2-isopropyl-1-oxo-1,2-dihydroisoquinolin-3-yl]ethen-1-yl]-3,4,5,6-tetrahydro-2H-pyran;

(2RS,4R,6S)-(E)-2,4-dihydroxy-6-[2-(2-(4-fluorophenyl)-4-isopropyl-1-oxo-1,2-dihydroisoquinolin-3-yl)ethen-1-yl]-3,4,5,6-tetrahydro-2H-pyran;

(4R,6S)-(E)-4-hydroxy-6-(2-(2-(4-methoxyphenyl)-4-isopropyl-1-oxo-1,2-dihydroisoquinolin-3-yl)ethen-1-yl)-3,4,5,6-tetrahydro-2H-pyran-2-one;

(2RS,4R,6S)-(E)-2,4-dihydroxy-6-(2-(4-isopropyl-2-(4-methoxyphenyl)-1-oxo-1,2-dihydroisoquinolin-3-yl)ethen-1-yl)-3,4,5,6-tetrahydro-2H-pyran;

(4R,6S)-(E)-6-(2-(2-(4-fluoro-3-methylphenyl)-4-isopropyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-2,4-dihydroxy-6-(2-(2-(4-fluoro-3-methylphenyl)-4-isopropyl-1-oxo-1,2-dihydroisoquinolin-3-yl)ethen-1-yl)-3,4,5,6-tetrahydro-2H-pyran;

(4R,6S)-(E)-6-(2-(2-(4-chlorophenyl)-4-isopropyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-(4-chlorophenyl)-4-isopropyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-(3,5-dimethylphenyl)-4-isopropyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-(3,5-dimethylphenyl)-4-isopropyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-(4-fluorophenyl)-4-methyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-(4-fluorophenyl)-4-methyl-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-cyclopropylmethyl-4-(4-fluorophenyl)-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-cyclopropylmethyl-4-(4-fluorophenyl)-1-oxo-1,2-dihydroisoquinolin-3-yl)ethen-1-yl)-2,4-dihydroxy-3,4,5,6-tetrahydro-2H-pyran;

(4R,6S)-(E)-6-(2-(2-cyclohexyl-4-isopropyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-cyclohexyl-4-isopropyl-1-oxo-1,2-dihydroisoquinolin-3-yl)ethen1-yl)-2,4-dihydroxy-3,4,5,6-tetrahydro-2H-pyran;

(4R,6S)-(E)-6-(2-(2-cyclohexylmethyl-4-isopropyl-1-oxo-1,2-dihydroisoquinolin-3-yl)ethen-1-yl)-4-hydroxy-3,4,5,6-tetrahydro-2H-pyran-2-one;

(2RS,4R,6S)-(E)-6-(2-(2-cyclohexylmethyl-4-isopropyl-1-oxo-1,2-dihydroisoquinolin-3-yl)ethen-1-yl)-2,4-dihydroxy-3,4,5,6-tetrahydro-2H-pyran;

(4R,6R)-(E)-4-hydroxy-6-[2-(4-(4-fluorophenyl)-2-isopropyl-1-oxo-1,2-dihydroisoquinolin-3-yl)ethen-1-yl]-3,4,5,6-tetrahydro-2H-pyran-2-one;

(2RS,4R,6R)-(E)-2,4-dihydroxy-6[2-{4-(4-fluorophenyl)-2-isopropyl-1-oxo-1,2-dihydroisoquinolin-3-yl}ethen-1-yl]-3,4,5,6-tetrahydro-2H-pyran;

sodium (3R,5S)-(E)-3,5-dihydroxy-7-(4-(4-fluorophenyl)-2-isopropyl-1-oxo-1,2-dihydroisoquinolin-3-yl)-hept-6-enoate;

sodium (3R,5S)-(E)-3,5-dihydroxy-7-(2-(4-fluorophenyl)-4-isopropyl-1-oxo-1,2-dihydroisoquinolin-3-yl)hept-6-enoate;

(4R,6R)-6-[2-{2-(4-fluorophenyl)-4-isopropyl-1-oxo-1,2-dihydroisoquinolin-3-yl}ethyl]-4-hydroxy-3,4,5,6-tetrahydro-2H-pyran-2-one; and (4R,6R)-6-(2-(4-(4-fluorophenyl)-2-isopropyl-1-oxo-1,2-dihydroisoquinolin-3-yl)ethyl)-4-hydroxy-3,4,5,6-tetrahydro-2H-pyran-2-one.

17. A pharmaceutical composition useful in the treatment of hypercholesterolaemic and hyperlipoproteinaemic states, of atherosclerosis and associated conditions and of fungal infections which comprises, as active ingredient, an effective amount of an isoquinolinone derivative of general formula I as defined in claim 1, or a pharmaceutically acceptable salt thereof, in association with a pharmaceutically acceptable carrier or coating.

* * * * *